US005847077A

United States Patent [19]

Green et al.

[11] Patent Number: 5,847,077

[45] Date of Patent: Dec. 8, 1998

[54] FUNGAL MULTISUBUNIT PROTEIN COMPLEX CRITICAL FOR EXPRESSION OF FUNGAL PROTEINS

[75] Inventors: Michael R. Green, Boylston; Joseph C. Reese, Jr., Shrewsbury, both of Mass.

[73] Assignee: University of Massachusetts Medical Center, Worcester, Mass.

[21] Appl. No.: 308,818

[22] Filed: Sep. 19, 1994

[51] Int. Cl.[6] .......................... C07K 14/39; C07K 4/06; C07K 7/04; C07K 14/37

[52] U.S. Cl. .......................... 530/350; 530/300; 530/324; 530/325; 530/326; 530/327; 530/328; 530/329; 530/330; 530/350

[58] Field of Search .......................... 530/324, 325, 530/326, 327, 328, 350, 329, 330, 300; 435/183

[56] References Cited

PUBLICATIONS

Auble, D.T. & Hahn, S., *Genes & Dev.,* 7:844–856 (1993).
Chien et al. (1991) *Proc Natl Acad Sci USA* 88:9578–9582.
Colbert, T. & Hahn, S., *Genes & Dev.,* 6:1940–1949 (1992).
Eisenmann, D. M.et al., *Genes & Dev.,* 6:1319–1331 (1992).
Fields and Song (1989) *Nature* 340: 245–246.
Ha, I. et al., *Genes & Dev.,* 7:1021–1932 (1993).
Hernandez, N., *Genes & Dev.,* 7:1291–1308 (1993).
Hisatake, K. et al., *Nature*, 362:179–181 (1993).
Inostraoza, J. A.et al., *Cell*, 70:477–489 (1992).
Kassavetis, G. A. et al., *Cell*, 71:1055–1064 (1992).
Kim, Y. J., et al., *Cell*, 77:599–608 (1994).
Kokubo, T., et al., *Genes & Dev.,* 7:1033–1046 (1993).
Koleske, A. J. & Young, R. A., *Nature*, 368:466–469 (1994).
Koleske, A. J. et al., *Cell*, 69:883–894 (1992).
Lopez–de–Leon et al., *Cell*, 71:211–220.
Manley et al. (1980) *Proc.Natl.Acad.Sci.USA* 77:3855–3859.
Meisterernst, M. et al., *Cell*, 66:981–993 (1991).
Meisterernst, M. & Roeder, R. G., *Cell*, 67:557–567 (1991).
Merino, A. et al., *Nature*, 365:227–232 (1993).
Pinto, I., Ware, D. E. & Hampsey, M., *Cell*, 68:977–988 (1992).
Poon, D. & Weil, P. A., *J. Biol. Chem.,* 268:15325–15328 (1993)*.
Poon, D. et al, *J. Biol. Chem*, 269:23135–23140 (1994)*.
Pugh,B. F. & Tijan, R., *J. Biol. Chem.,* 267:679–682 (1992).
Ruppert, S., Wang, E. H. & Tijan, R. *Nature* (*London*) 362, 175–179 (1993).
Berger et al., *Cell*, 70:251–265 (1992).
Sharp, P. A., *Cell*, 68:819–821 (1992).
Tam(1988) *Proc Natl Acad Sci USA* 85, 5409–5413.
Thompson, C. M. et al., *Cell*, 73:1361–1375 (1993).
Verrijzer, C.P. et al., *Science*, 264:933–941 (1994)*.
Woontner, M., et al. *Mol. Cell. Biol.* 11, 4555–4560 (1991).
Zhou, Q., Boyer, T. G. & Berk, A. J., *Genes & Dev.,* 7:180–187 (1993).

*Primary Examiner*—James Ketter
*Assistant Examiner*—Terry A. McKelvey
*Attorney, Agent, or Firm*—Darby & Darby

[57] ABSTRACT

The present invention provides a complex of fungal polypeptides, termed TAFs, that are necessary for activated transcription in fungi such as *S. cerevisiae*. The complex comprises at least nine associated subunit polypeptides, having molecular masses of about 180 kDa, 145 kDa, 116 kDa, 90 kDa, 68 kDa, 51–54 kDa, 47 kDa, and 30 kDa, respectively. TAF-145, having the sequence set forth in FIG. 6B, binds TATA-box Binding Protein (TBP). The invention also includes nucleic acid sequences encoding TAF-145, as well as DNA vectors and transformed cells suitable for recombinant expression of this polypeptide.

5 Claims, 19 Drawing Sheets

GST-yTBP FT
WCE
FRACTION
GAL4-VP16
1 2 3 4 5 6 7 8 9 10
GAL4
cyc1
G-less cassette
pCGC-

FIG. 6B

| FIG. 6B1 | FIG. 6B2 | FIG. 6B3 |
| --- | --- | --- |
| FIG. 6B4 | FIG. 6B5 | FIG. 6B6 |

FIG. 6A

| FIG. 6A1 | FIG. 6A2 | FIG. 6A3 |
| --- | --- | --- |

FIG. 6A1

```
yTAF90 1 MSQKQSTNQNQNGTHQPQPVKNQRTNNAAGANSGQQPQQQSQGQSQQQGRSN.GPFSASD 59
         ||  .  |.  ...|||: .:. ::   .       .  .  ..  ::   .|...  :.  :  :.:|.||
dTAF80 1 MSLEVSNINGGNGTQLSHDKRELLCLLKLIKKYQLKSTEELLCQEANVSSVELSEISESD 60

      60 LNRIVLEYLNKKGYHRTEAMLRAESGRTLTPQNKQSPANTKTGKFPEQSSIPPNPGKTAK 119
         :..:: . |.  : :|.   :.....     .. .:. |...  :||  ::.|:
      61 VQQVLGAVLGAGDANRERKHVQSPAQGHKQSAVTEANAAEELAKFIDDDSF......... 111

     120 PISNPTNLSSKRDAEGGIVSSGRLEGLNAPENYIRAYSMLKNWVDSSLEIYKPELSYIMY 179
                                     .:::|  .||.  |:.:|:.||:|||.|||  ::|
     112 ............................DAQHYEQAYKELRTFVEDSLDIYKHELSMVLY 143

     180 PIFIYLFLNLVAKN.PVYARRFFDRFSPDFKDFHGSEINRLFSVNSIDHIKENEVASAFQ 238
         ||:: :::.::|.. .  |: |::::..|:.::. .:: .|: :.. :.: ||::. |::
     144 PILVQIYFKILASGLREKAKEFIEKYKCDLDGYYIEGLFNLLLLSKPEELLENDLVVAME 203

     239 SHKYRITMSKTTLNLLLYFLNENESIGGSLIISVINQHLDPNIVESVTAREKLADGIKVL 298
          .|: | ||:.. .|:   :.:.    ..:: .::...|. :. |:: ||:||   .. .
     204 QDKFVIRMSRDSHSLFKRHIQDRR...QEVVADIVSKYLHFDTYEGM.ARNKL..QCVAT 257
```

FIG. 6A2

```
299 SDSENGNGKQNLEMNSVPVKLGPFPKDEEFVKEIETELKIKDDQEKQLNQQTAGDNYSGA 358
     .:|. |::|..                                  :..:::  :  |::: || ..  .::
258 AGSHLGEAKRQ.......................DNKMRVYYGLLKEVDFQTLTTPAPAP 294

359 NNRTLLQEYKAMNNEKFKDNTGDDDKDKIKDKIAKDEEKKESELKVDGEKKDSNLSSPAR 418
    :                    ::||... .|: |...||:. |   :.|..|: ..|.
295 E.....................EEDDDPDAPDRPKKKKPKKDPLL...SKKSKSDPNAPSI 331

419 DILPLPPKTALDLKLEIQKVKESRDAIKLDNLQLALPSVCMYTFQNTNKDMSCLDFSDDC 478
    | :|||. .. |  |.:. ::|... : |.. |  |||..:||. |.:.::.| ::|||:
332 DRIPLPELKDSDKLLKLKALREASKRLALSKDO..LPSAVFYTVLNSHOGVTCAEISDDS 389

419 DILPLPPKTALDLKLEIQKVKESRDAIKLDNLQLALPSVCMYTFQNTNKDMSCLDFSDDC 478
    | :|||. .. |  |.:. ::|... : |.. |  |||..:||. |.:.::.| ::|||:
332 DRIPLPELKDSDKLLKLKALREASKRLALSKDQ..LPSAVFYTVLNSHQGVTCAEISDDS 389

479 RIAAAGFQDSYIKIWSL.........DGSSL.....NNPNIALNNNDKDEDPTCKTLVGH 524
     : |.||.|| ::||||         |:.||     :.::|.:. |. .:...:.|:||
390 TMLACGFGDSSVRIWSLTPANVRTLKDADSLRELDKESADINVRMLDDRSGEVTRSLMGH 449
```

FIG. 6A3

```
525 SGTVYSTSFSPDNKYLLSGSEDKTVRLWSMDTHTALVSYKGHNHPVWDVSFSPLGHYFAT 584
    .|.||...|.|: ..|||.|||.|:||||: | ..:|.|:|| .|||||.|.| |.||..
450 TGPVYRCAFAPEMNLLLSCSEDSTIRLWSLLTWSCVVTYRGHVYPVWDVRFAPHGYYFVS 509

585 ASHDQTARLWSCDHIYPLRIFAGHLNDVDCVSFHPNGCYVFTGSSDKTCRMWDVSTGDSV 644
    .|.|.||||||..|    :||:|.|||.||||| ||||: || |||||:|.|:||  ||:||
510 CSYDKTARLWATDSNQALRVFVGHLSDVDCVQFHPNSNYVATGSSDRTVRLWDNMTGQSV 569

645 RLFLGHTAPVISIAVCPDGRWLSTGSEDGIINVWDIGTGKRLKQMRGHGKNAIYSLSYSK 704
    ||: ||.:.| |:|.:: ||:|..|| |   | :||::.|. :. :  |. ..: .:.:|:
570 RLMTGHKGSVSSLAFSACGRYLASGSVDHNIIIWDLSNGSLVTTLLRHT.STVTTITFSR 628

705 EGNVLISGGADHTVRVWDLKKATTEPSAEPDEPFIGYLGDVTASINQDIKEYGRRRTVIP 764
    :|.|| .:| |:.: :||:.|.|           |.:|:  ..:|.| :|| .:       .
629 DGTVLAAAGLDNNLTLWDFHKVT........EDYIS..NHITVSHHQDEND........E 670

765 TSDLVASFYTKKTPVFKVKFSRSNLALAGGAFRP 798
    .  |: .| .|..|...:.|.|.|| :..| |:.
671 DVYLMRTFPSKNSPFVSLHFTRRNLLMCVGLFKS 704
```

FIG. 6B1

```
yTAF145 1  MVKQQGSGKTNLANEDEAYEAIFGGEFGSLEIGSYIGGDEGA.
           | .:.:.:...::|: : ..:|: |:::|   |..:.:|:|.
dTAF250 3  MESDNSDDEGSIGNGLD.LTGILFGNIDS..EGRLLQDDDGEG

        73 ESDANLHPAMMTMGAYDDVN........ENGAVLGIDSNSLNM
           :. :.  .|  .|:|:|.:.        |:||| : |..
        88 DARPSAVSASGGMSAFDALKAGVKREEREDGAVKAQDDAIDYS

       149 ETGVLDGSGANEIGHSQLSIGGVNGNDMSINGGFIMEPDMSDG
           ..:.: ::::.:|:... |       || |  ::  ...| .|:
       177 PSAPMRSGSGGGIEEPAKS......NDASSPSDDSKSTDSKDA

       228 ...IYRRSVPYHWHSEISRVKKPF...............MPL
              |:|:  . ::..: || .|.                ..:
       261 LPQIWRHVRKRRRKRNQSRDQKTTNTGGSDSPSDTEEPRKRGF

       288 SSASRRGLIHVSIDEL..........FPIK........EQQKK
            ...| |  ::..| |          :.:|        :|| |
       350 VADWRFGPAQIWYDILEVPDSGEGFNYGFKTKAASTSSQQQLK

       339 .INQGTSSTATLADS.SMT.........PNLKF........SG
            :|  |...: |:.| |.|          |.:..          ||
       440 KLNSKTNAAGWLPSSGSRTAGAFSQPGKPSMPVGSGSSKQGSG

       388 ...KLKESKHAELNMNDEKLLLMI......EKTN.........
              |:...|  .|: |||.::| |      .|.|
       530 QVSKVPKPKVLTLDPNDENIILGIPDDIDPSKINKSTGPPPKI
```

FIG. 6B2

```
447 YQILKKTHQTKVRSTISNLNIQHSQPAINLQSPFYKVAVPRYQ
    |   .||..| :| .::.  |||| |.::|..|| .. :.. .
620 Y..TPKTEPT.LRLKVGGNLIQHSTPVVELRAPFVPTHMGPMN

532 TSQDLTI........GDTAPVYLMEYSEQTPVALSKFGMANKL
    .:.|: :        | .:.: | |::|: |. :...||..|:
706 GGGDVFFMRNPEDLSGRDGDIVLAEFCEEHPPLINQVGMCSKI

614 LYNNMIRAPVFKHDISGTDFLLTKSSGFGISNRFYLRNINHLF
    : |||.|||::.|.:. .|||:.:.     .|.:::|.:| ::
791 IENNMYRAPIYPHKMAHNDFLVIRT.....RNNYWIRSVNSIY

702 DPIAKHFPDQDYGQNRQKVKEFMKYQRDGPEKGLWRLKDDEKL
    |.| . ||.:. : |.::|:  .:.|.| :..:| :|.: :|
876 DDIKQAFPAHSESSIRKRLKQCADFKRTGMDSNWWVIKPEFRL

778 YNFDSKLKSLEE.NLLPWNITKNFINSTQMRAMIQIHGVGDPT
      :..||  :| .: |||.|:.:|.. . :.::|: |.:|||
966 ...EAQLKLDDEVKVAPWNTTRAYIQAMRGKCLLQLSGPADPT
```

FIG. 6B3
```
837  ...........VKSGSP..........SSNNNSSNKKGTNTHS
                :|. |.          |.:.......| :. |
1053 LLRQFKVPEEEIKKLSRWEVIDVVRTLSTEKAKAGEEGMDKFS
888  .PFEEMTNPDEINQTNKHVKT.....................
      .:||:..  |   .||...|
1143 SDLEELGKNLENMLSNKKTSTQLSREREELERQELLRQLDEEH
931  QTIFIRDPRVIQGYIKIKEQDKEDVNKLLEEDTSKINNLEELE
     ..  :| ..||::||||:. ..|:. | :  .| . .. ||:.
1233 RVETVRRQPVIDAYIKIRTTKDEQFIKQF..ATLDEQQKEEMK
1018 .......LAGVTDGKAARNKGK...NTTRRCATCGQIGHIRTN
            .| .:..:.|.| |   : . :|:.|||:||:|||
1321 GHSHKERDSGYKEVSPSRKKFKLKPDLKLKCGACGQVGHMRTN
```
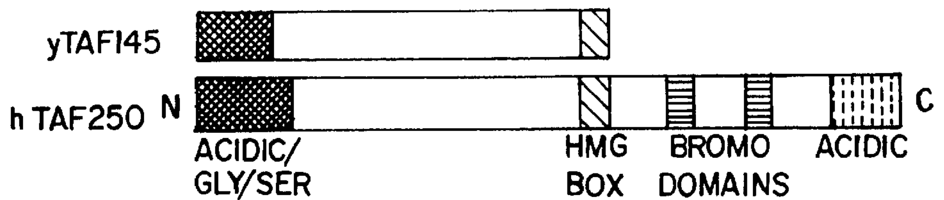

FIG. 6B4

```
.NSKDYTEHLP................DAVDFEDEDELADDDDDLPE  72
 .:.::...|.                :.:|:.:.:.  .||:::  |
RGGTGFDAELRENIGSLSKLGLDSMLLEVIDLKEAEPPSDDEEE..E  87

QLPEINGD.....LSQQFILED.DGGTPATSNALFMGMDANEIHLAT 148
::.|:.:|       .:  ..:| :::.||.. .  :..|..|: ::.
DITELSEDCPRTPPEETSTYDDLEDAIPASKVEAKLTKDDKEL.MPP 176

KHKKATKLDLINHEKYL...LKKYFPDFEKGKILKWNKL........ 227
.:| .|.|. | ..||    ::..|||| ..|:|::.:|
DRKLDTPLADILPSKYQNVDVRELFPDFRPQKVLRFSRLFGPGKPTS 260

NLKFKVQ........QDDKRL...FNSRTISYVAPIYQGKNNLLQSN 287
.|.: .:        :|:.:|   ||| .:.  :|  .|.|.  ...
SLHYAAEPTPAECMSDDEDKLLGDFNSEDVRPEGPD.NGENSDQKPK 349

..RKIIH.....DEKTISED..LLIATDDWDQEKI............ 338
  |::       ::..|.:|  |::.  .|::: :
DERRVKSPEDDVEDPSIADDAFLMVSQLHWEDDVVWDGNDIKAKVLQ 439

GYKLK..................SLIEDVAED...WQWDEDMIIDA. 387
: . |                  ||:.  .|:   :.|::::| ||
ASSKKAQQNAQAKPAEAPDDTWYSLFPVENEELIYYKWEDEVIWDAQ 529

.....NLAQQKQQLDSSNLILPLNETIL........QQKFNLSNDDK 446
    :: . |  |:...:| .|.|..          .:.||:|||.
KIPHPHVKKSKILLGKAGVINVLAEDTPPPPPKSPDRDPFNISNDTY 619
```

FIG. 6B5

```
LRHFHRENFG..SHIRPGTKI...VFSKLKARKRKRDKGKDVKESFS  531
:| |||. :    || . : .|   ||. ||.   |:.|.::|.   |
VRAFHRPPLKKYSHGPMAQSIPHPVFPLLKTIA.KKAKQREVERIAS  705

INYYRKANEQDTLRPKLPVGETHVLGVQDKSPFWNFGFVEPGHIVPT  613
 |||:: .|.|. ..... ||   ::....|||  :|::.||:.:..
KNYYKRKAEKDSGPQDYVYGE...VAFAHTSPF..LGILHPGQCIQA  790

TVGQTFPVEEIPGPNSRKVTSMKATRLKMIIYRIL..NHNHSKAISI  701
||||. |: |:||||||::...:. . |.::|||::  .:::.: |.:
TVGQECPLYEVPGPNSKRANNFTRDFLQVFIYRLFWKSRDNPRRIRM  875

LDNEAVKSLITPEQISQVESM............SQGLQF..QEDNEA  777
 .:|.::.::.|||.:.   ||             :: : |  |||::.
PSEEEIRAMVSPEQCCAYFSMIAAEQRLKDAGYGEKFLFAPQEDDDE  965

GCGEGFSFLK....................ISMKGGF..........  836
|||||||:::                    |: .:::
GCGEGFSYVRVPNKPTQTKEEQESQPKRSVTGTDADLRRLPLQRAKE  1052
```

FIG. 6B6

```
....YNVAQQQKAYDEEIAKTWYTHTKSLSISN.............. 887
    :.:|::|. |.||..:.:  :.: |. |:
RGNRFSIAEHQERYKEECQRIFDLQNRVLASSEVLSTDEAESSASEE 1142

.............DRDDK...........KILKIVRKKRDENGIIQR 930
             ::||.           :||:|.|. |:::|
GGPSGSGGAKGAKGKDDPGQQMLATNNQGRILRITRTFRGNDGKEYT 1232

KQKKLLQLELANLEKSQQR.RAAR..QNSKRNGGATRTENSVDNGSD 1017
::|: :| :| .:.:.|:| | |.  || | ..|: .|. : ..:|:
REKRRIQEQLRRIKRNQERERLAQLAQNQKLQPGGMPTSLGDPKSSG 1320

KSCPMYSSKDNPASPK 1066
|.||:||:.:.. |..
KACPLYSGMQSSLSQS 1379
```

FUNGAL MULTISUBUNIT PROTEIN COMPLEX CRITICAL FOR EXPRESSION OF FUNGAL PROTEINS

FIELD OF THE INVENTION

This invention pertains to proteins required for activated transcription in yeast and fungi, nucleic acids encoding these proteins, and methods of using these proteins.

BACKGROUND OF THE INVENTION

Most fungi are opportunistic pathogens, producing serious disease only in compromised individuals. As the result of an aging population and an increase in the number of immunocompromised patients, specifically patients with acquired immunodeficiency syndrome (AIDS), patients undergoing cancer, and corticosteroid therapy, as well as in patients undergoing organ transplantation, fungal infections are increasing rapidly.

Most infections begin by colonization of either the skin, a mucosal membrane, or the respiratory epithelium. Passage through the initial surface barrier is accomplished through a mechanical break in the epithelium or enzymatic degradation or spore dissemination. Most fungi are readily killed by neutrophils and are only opportunists, but some species are resistant to phagocytic killing and may infect otherwise healthy individuals.

Fungi parasitize many different tissues. Superficial fungi cause indolent lesions of the skin. Subcutaneous pathogens cause infection through the skin and spread by subcutaneous or lymphatic routes. Opportunistic fungi such as Aspergillus are widespread in the environment and are present in normal flora and cause disease mostly in immunocompromised individuals. Systemic fungi are the most virulent and may cause progressive disease leading to deep seated visceral infections in otherwise healthy individuals (see e.g. *Sherris Medical Microbiology*, Third Edition, Kenneth J. Ryan, ed., Appleton & Lange, Norwalk, Conn., 1994).

The major fungal pathogens in North America are *Histoplasma capsulatum, Coccidioides immitis, Blastomyces dennatitidis, Cryptococcus neofornans*, Candida species and Aspergillus species (*Medically Important Fungi*, Second Edition, Davise H. Larone, Ed., American Society for Microbiology, Washington, D.C.). *Histoplasma capsulatum* causes histoplasmosis, which may be chronic or progressive and fatal. It is either a localized or disseminated infection, primarily of the reticuloendothelial system. *Coccidioides immitis* causes coccidioidomycosis, a highly infectious disease that is endemic to the southwestern United States and may be a chronic, sometimes fatal infection involving the skin, bone, joints, lymph nodes, adrenal glands and central nervous system. *Blastomyces dermatitidis* causes blastomycosis, a chronic infection characterized by suppurative and granulomatous lesions that begins in the lungs and is disseminated to the skin and bones. *Cryptococcus neoformans* causes cryptococcosis, which may be a chronic infection involving the central nervous system. *Candida albicans* is the most frequent cause of candidiasis, which ranges from an acute to a chronic infection involving any part of the body. *Aspergillus fumigatus* is one of the most frequent causes of aspergillosis, which is an opportunistic infection in immunosuppressed individuals.

Fungi are a distinct class of microorganism, most of which are free-living. They are eukaryotic organisms containing a nuclear membrane, mitochondria and an endoplasmic reticulum. The cell structure includes a rigid cell wall of mannan, glucan, and chitin and a cytoplasmic membrane with a large percentage of ergosterol. The size and morphology of fungi vary. There are monomorphic yeasts and yeast-like organisms including Candida, Cryptococcus, and Saccharomyces. There are monomorphic molds, such as Aspergillus and Coccidiodes. Some thermally dimorphic fungi, such as *Blastomyces dermatitidis* and *Histoplasma capsulatum*, grow either in a yeast or mold phase.

Only a handful of agents are active against fungi. For life threatening disease caused by any of these fungi, amphotericin B is the agent of choice. This drug, however, is associated with numerous severe side effects such as fever, dyspnea and tachycardia, and dosage is limited over the lifetime of the patient because of renal toxicity. An agent frequently used concurrently is flucytosine, a nucleoside analog that cannot be used independent of other agents because of the rapid appearance of resistance. Untoward effects of treatment with flucytosine include leukopenia, thrombocytopenia, rash, nausea, vomiting, diarrhea, and severe enterocolitis.

In conditions where the patient's life is not threatened, ketoconazole can be used as a long-term therapy for blastomycosis, histoplasmosis, or coccidioidomycosis. Fluconazole also has a significant role in the treatment of superficial fungal infections. Both compounds are from the same class, the triazoles, and are cytostatic. The emergence of resistance and hepatic toxicity limit the use of triazoles such as fluconazole and ketoconazole. The newest triazole, itraconazole, has similar pharmacokinetics and spectrum of activity as fluconazole. None of the azoles can be used for life threatening or deep seated fungal infections, but they are effective in reducing colonization of fungi such as Candida and for treating superficial mycoses.

All major antifungal agents attack directly or indirectly a component of the cell wall--ergosterol. Amphotericin B and other polyene macrolides interact with ergosterol in the cell membrane and form pores or channels that increase the permeability of the membrane. Resistant to amphotericin B in mutant strains is accompanied by decreased concentrations of ergosterol in their cell membranes. Imidazoles and triazoles inhibit sterol 14-α-demethylase, a microsomal cytochrome $P_{450}$-dependent enzyme system. Imidazoles and triazoles thus impair the biosynthesis of ergosterol for the cytoplasmic membrane and lead to the accumulation of 14-α-methyl sterols, which impair certain membrane-bound enzyme systems (See e.g. *The Pharmacological Basis of Therapeutics*, Eighth Edition, Goodman and Gilman, Pergamon Press, 1990).

Development of an effective method and composition for treatment of fungal infections is a critical goal of the pharmaceutical industry. The pharmaceutical industry has made numerous efforts to identify fungal-specific drugs, with only limited success to date. It would be of great value to identify a new class of antifungal drug that blocks a fungal target other than ergosterol. This target should be fungal-specific and should lead to development of a drug that is effective against the organisms that are resistant to current therapy.

Drug development often relies on the screening of a large number of potential inhibitors before a specific lead compound inhibitor is found. Assays developed for such screens are complex and must mimic the physiological activity of the target protein. Thus, it is critical for the development of these screens to define the proteins involved in the targeted process and to have discovered a means of purifying the necessary components of the assay for use in the assay. In addition, it is useful to have clones for the protein components of the assay to facilitate the production of the components.

Therefore, there is a need in the art to identify one or more fungal constituents, preferably polypeptides, that can serve as useful targets for drug intervention, and for methods and compositions for identifying useful anti-fungal agents and treating fungal infections.

SUMMARY OF THE INVENTION

The present invention provides a complex of fungal polypeptides, termed TAFs, that are necessary for activated transcription in fungi such as *S. cerevisiae*. The complex comprises at least nine associated subunit polypeptides, having molecular masses of about 180 kDa, 145 kDa, 116 kDa, 90 kDa, 68 kDa, 51–54 kDa, 47 kDa, and 30 kDa, respectively. TAF-145, having the sequence set forth in FIG. 6B Seq. ID No: 1 binds TATA-box Binding Protein (TBP). The invention also includes nucleic acid sequences encoding TAF-145, as well as DNA vectors and transformed cells suitable for recombinant expression of this polypeptide.

In one aspect, the present invention encompasses methods for inhibiting fungal transcription in a fungal cell, comprising contacting the cell with an agent that selectively interferes with the transcriptional activation activity of the yeast TAF complex.

In another aspect, the invention provides a method for high-throughput screening of large numbers of test compounds, to identify an agent useful in the treatment of fungal diseases in mammals. The method is carried out by exposing the TAF complex or TAF-145 to TBP in the presence of at least one test compound, followed by identifying those test compounds that inhibit the binding of TBP to the TAF complex or TAF-145.

BRIEF DESCRIPTION OF THE DRAWINGS

FIG. 6A shows the deduced amino acid sequence of yeast TAF-90 SEQ ID NO: 2 polypeptide and a comparison with the sequence of drosophila TAFII-80 SEQ ID NO: 3.

FIG. 6B shows the deduced amino acid sequence of yeast TAF-145 SEQ ID NO: 1 and a comparison with the sequence of drosophila TAFII-250 SEQ ID NO: 4.

DETAILED DESCRIPTION OF THE INVENTION

Figure 1:
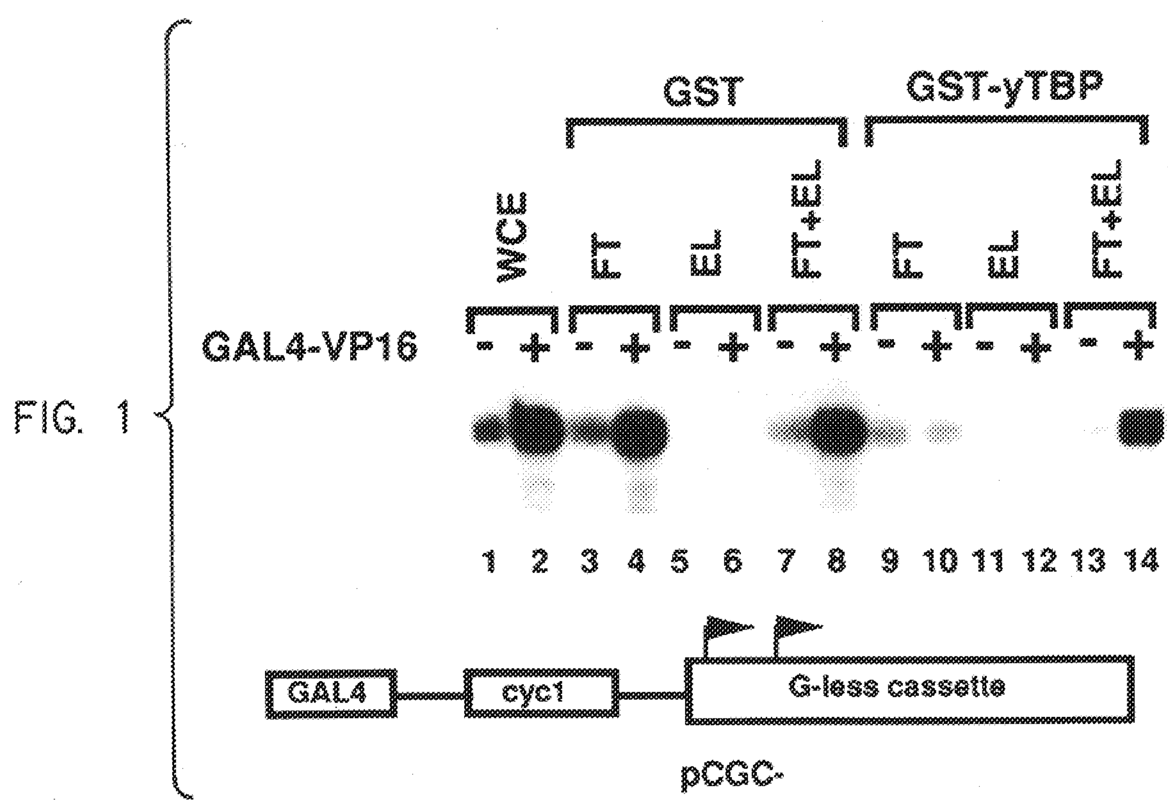
FIG. 1 shows transcriptional activation reactions programmed by the DNA template shown in the bottom of the figure. The reactions contained either a yeast whole cell extract (WCE), or the flow-through (FT) or eluate (EL) fractions of column chromatography of the WCE on glutathione-S-transferase (GST) columns or on columns containing TATA-box Binding Protein (TBP) coupled to GST. The GAL 4 activator protein was added as indicated.

All patent applications, patents, and literature references cited in this specification are hereby incorporated by reference in their entirety. In case of conflict, the present description, including definitions, will control.

Definitions:

1. "Basal transcription" refers to transcription activity from an RNA polymerase II-directed promoter in the absence of an upstream transcriptional activator.

2. "Coactivator activity" refers to the activity that allows an upstream transcription factor such as GAL4 or its derivatives to activate transcription from an RNA polymerase II-directed promoter in an in vitro or in vivo reconstituted transcription system. Coactivator activity is further defined as an activity that has no effect on basal transcription.

3. "TATA-box binding protein" or "TBP" is a major component of eukaryotic transcription factors. In higher eukaryotes, TBP is isolated as part of a larger protein complex (see below).

4. "TATA-box binding protein- associated factors" or "TAFs" as used herein refer to polypeptides or complexes of polypeptides required for "coactivator activity" in fungal RNA polymerase 11 transcription reactions by virtue of their association with TBP.

5. "Functional homology" between TAF polypeptides or complexes of polypeptides indicates that one or more biochemical properties specific to fungal TAFs are shared. Examples of such properties are: the ability to specifically modulate the transcription from RNA polymerase II-directed promoters in the presence of an upstream activator protein, and the capacity to specifically bind TBP as a multisubunit complex or as a single subunit under conditions as described herein.

6. "Sequence homology" is used herein to describe the relatedness of TAFs from different sources. "Substantial" sequence homology means that about 70%, more preferably at least about 80%, and most preferably at least about 90% of the two sequences are identical. The level of sequence homology may also be defined functionally, as in, e.g. the stringency of hybridization conditions under which the two sequences effectively or substantially hybridize. "Stringent" hybridization conditions are defined herein as 0.1×SSC at 65° C.

7. "TAF subunits" refers to individual polypeptides that comprise the TAF complex. Such polypeptides are distinguished from any polypeptides previously known to be TBP binding proteins. Fungal TAF subunits may be recombinant or purified from natural sources, and may include structural or functional TAF homologues as defined above.

8. A "fungal-specific epitope" of a fungal TAF subunit comprises a three-dimensional structural conformation presented by a folded or assembled TAF polypeptide that is not presented by the homologous mammalian sequence.

8. "Modulating transcription" means altering transcription, and includes increasing or decreasing the rate or level of transcription and changing the responsiveness of transcription to regulatory controls.

9. An "isolated" polypeptide or nucleic acid is defined as one that is unaccompanied by at least some of the material with which it is associated in its natural state. Generally, an isolated polypeptide constitutes at least about 1%, preferably at least about 10%, and more preferably at least about 50% by weight of the total protein in a given sample. Included in the polypeptide weight are alternative forms such as differentially glycosylated or phosphorylated or otherwise post-translationally modified forms. An "isolated" nucleic acid sequence is present as other than a naturally occurring chromosome or transcript in its natural state and typically is removed from at least some of the proteins with which it is normally associated with on a natural chromosome. A partially pure nucleotide sequence constitutes at least about 5%, preferably at least about 30%, and more preferably at least about 90% by weight of total nucleic acid present in a given fraction.

The present invention is based on the surprising finding that the yeast *Saccharomyces cerevisiae* contains "TATA-box binding protein-associated factors", or TAFs, which function in regulating the activity of RNA Polymerase II. Prior to the work reported herein (see Example 1 below), no biochemical or genetic evidence had indicated the existence of such polypeptides in yeast. The discovery and characterization of these polypeptide factors. and the elucidation of differences between their yeast and mammalian versions, implicate these proteins as important targets for the development of new methods and compositions for treatment of fungal infections. The present invention is thus directed towards selective interference with fungal TAF activity, under conditions in which there is no effect on mammalian TAF function.

TAF Complexes, Subunit Polypeptides, and Nucleic Acids

The present invention provides yeast TAFs, which comprise a complex of nine polypeptides, or closely related families of polypeptides, having molecular masses of about 180, 145, 116, 90, 68, 62, 51–54, 47, and 30 kDa. The complexes, and polypeptide components thereof, may be isolated by virtue of their affinity to fungal or human TBP (see Example 1 below), by the use of chromatographic procedures that take advantage of physico-chemical characteristics of the complexes or of individual subunits, or by affinity to TAF-specific antibodies. The isolated complexes may contain all, or only a subset, of the total known complement of TAF subunits. TAF multisubunit complexes may also be reconstituted and purified from translation products of subunit genes, or from recombinantly produced TAF subunits. It is also contemplated that additional TAF subunit polypeptides will be identified using methods disclosed herein, and will be used in practicing the present invention.

Figure 6C:
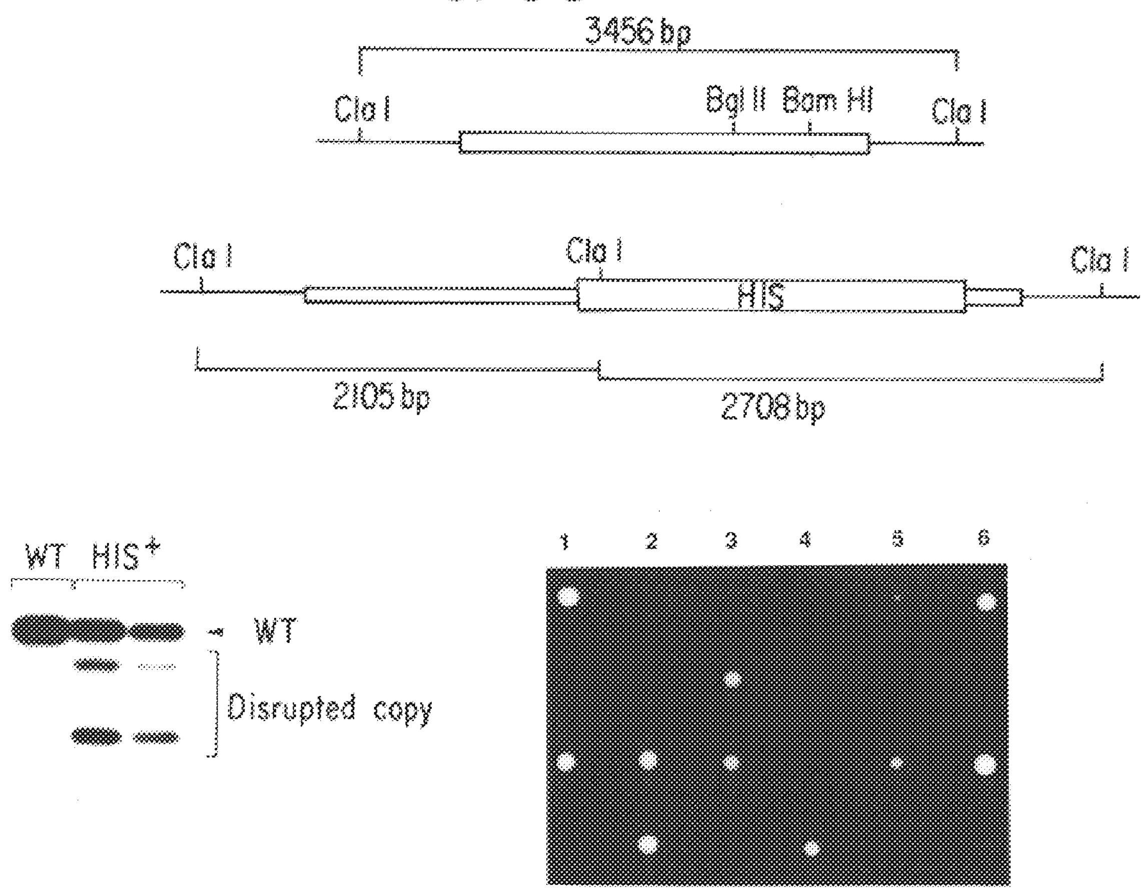
FIGS. 6C and 6d show the disruption of the yeast gene encoding TAF-90, and the disruption of TAF-145 (bottom), respectively. The DNA constructs containing disrupted copies of each gene are shown of each figure. At bottom left are shown Southern blots confirming correct integration of the disrupted gene within each endogenous gene. At bottom right are shown the growth patterns of spores dissected from each disrupted strain.
Figure 6D:
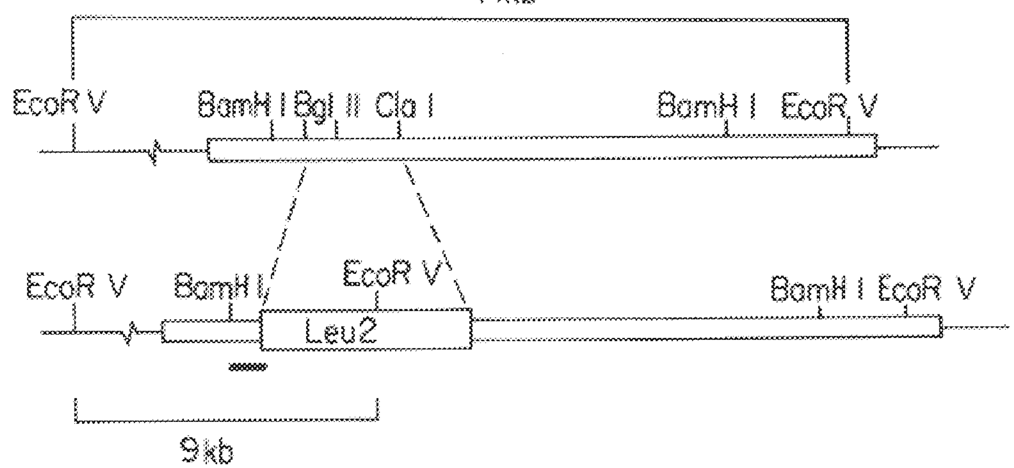
Figure 6D:
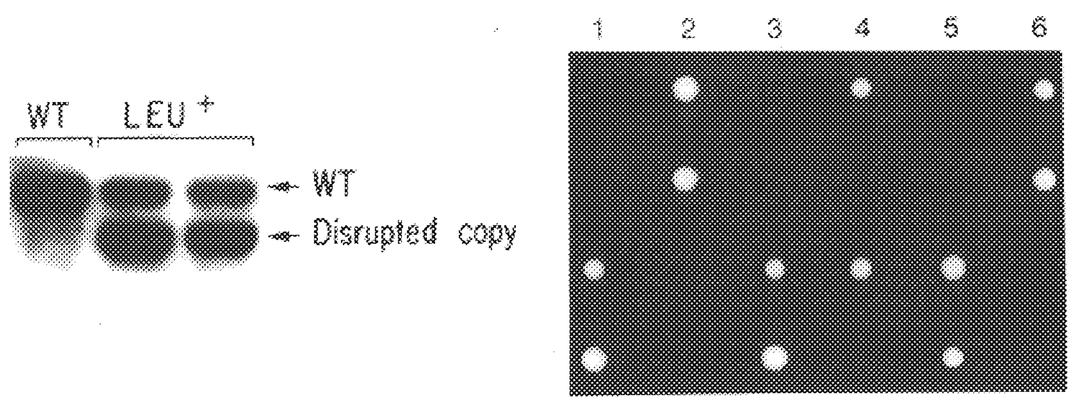

The present invention also encompasses nucleic acid sequences that encode TAF subunits. Methods for determining the relevant nucleic acid sequences are described in Example 1 below, and the deduced amino acid sequences of two TAF subunit genes, i.e. genes encoding the 90 kDa and 145 kDa TAF polypeptides (TAF-90 SEQ ID NO: 2 and TAF-145SEQ ID NO: 1, respectively), are shown in FIG. 6B. The present invention encompasses DNA and RNA sequences, and sense and antisense sequences. TAF-encoding sequences according to the present invention may be modified by transitions, transversions, deletions, insertions, or other modifications such as alternative splicing. The invention also encompasses genomic TAF sequences and TAF gene flanking sequences, including TAF regulatory sequences. Nucleic acid sequences encoding TAF polypeptides may also be associated with heterologous sequences, including promoters, enhancers, response elements, signal sequences, polyadenylation sequences, introns, 5'- and 3'-noncoding regions, and the like. Other useful heterologous sequences are known to those skilled in the art. Furthermore, the nucleic acids can be modified to alter stability, solubility, binding affinity and specificity. For example, TAF encoding sequences can be selectively methylated. The nucleic acid sequences of the present invention may also be modified with a label capable of providing a detectable signal, either directly or indirectly. Exemplary labels include radioisotopes, fluorescent molecules, biotin, and the like.

In general, nucleic acid manipulations according to the present invention use methods that are well known in the art, as disclosed in e.g. *Molecular Cloning, A Laboratory Manual* (2nd Ed., Sambrook, Fritsch and Maniatis, Cold Spring Harbor), or *Current Protocols in Molecular Biology* (Eds. Aufubel, Brent, Kingston, More, Feidman, Smith and Stuhl, Greene Publ. Assoc., Wiley-Interscience, NY, N.Y., 1992).

The invention also provides vectors comprising nucleic acids encoding TAF or TAF analogs. A large number of vectors, including plasmid and fungal vectors, have been described for expression in a variety of eukaryotic and prokaryotic hosts. Advantageously, vectors may also include a promotor operably linked to the TAF encoding portion. The encoded TAF may be expressed by using any suitable vectors and host cells, using methods disclosed or cited herein or otherwise known to those skilled in the relevant art. The particular choice of vector/host is not critical to the invention.

Vectors will often include one or more replication systems for cloning or expression, one or more markers for selection in the host, e.g. antibiotic resistance, and one or more expression cassettes. The inserted TAF coding sequences may be synthesized, isolated from natural sources, prepared as hybrids, etc. Ligation of the coding sequences to the transcriptional regulatory sequences may be achieved by known methods. Suitable host cells may be transformed/transfected/infected by any suitable method including electroporation, $CaCl_2$ mediated DNA uptake, fungal infection, microinjection, microprojectile, or other established methods.

Appropriate host cells included bacteria, archebacteria, fungi, especially yeast, and plant and animal cells, especially mammalian cells. Of particular interest are *E. coli*, B. Subtilis, *Saccharomvces cerevisiae*, SF9 cells, C129 cells, 293 cells, Neurospora, and CHO cells, COS cells, HeLa cells, and immortalized mammalian myeloid and lymphoid cell lines. Preferred replication systems include M13, Co1E1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced TAFs.

Nucleic acids encoding TAF polypeptides may also be introduced into cells by recombination events. For example, such a sequence can be microinjected into a cell, and thereby effect homologous recombination at the site of an endogenous gene encoding TAF, an analog or pseudogene thereof, or a sequence with substantial identity to an TAF-encoding gene. Other recombination-based methods such as nonhomologous recombinations, deletion of endogenous gene by homologous recombination, especially in pluripotent cells, may also be used.

TAF-containing complexes, the individual polypeptides contained therein, and the nucleic acids encoding these polypeptides may be derived from *S. cerevisiae*, or may be fungal, non-*S. cerevisiae*-derived proteins with substantial functional or sequence homology to *S. cerevisiae* TAFs. These TAFs may be derived from fungal sources such as *Histoplasma capsulatum, Coccidioides immitis, Blastomyces dermatitidis, Cryptococcus neoformans*, Candida species, and Aspergillus species such as *Aspergillus fumigatus*. Preferably the TAFs are derived from other yeast-like organisms such as Candida, and most preferably, *C. albicans*. Non-*S. cerevisiae* TAFs may be identified and isolated by methods that are well-known in the art. These include: antibody cross reactivity; PCR amplification from genomic DNA using degenerate oligonucleotide probes derived from the TAF sequences disclosed herein; low-stringency hybridizations using similar *S. cerevisiae* probes; and, finally, functional cloning, in which a cDNA expression library derived from another species is used to transform and complement an absent or defective TAF function in *S. cerevisiae.*

The present invention encompasses TAF complexes and subunits purified from wild-type and genetically altered strains of *S. cerevisiae*, as well as TAFs of all fungal origins recombinantly produced in a non-native context. In one embodiment, a baculovirus expression system permits the recombinant TAF to be modified, processed and transported within a eukaryotic system. In another embodiment, assembly of the TAF complex, or binding of preassembled TAF complexes to TBP, is performed in a reconstituted cell-free system using partially purified or substantially purified components. For example, TAF complexes, or components thereof, may be adsorbed to the surface of a microtiter plate, and incubated with radiolabelled TBP protein. Functional binding of TBP to TAF complexes or components will result in the association of detectable radioactivity with the plate.

TAF polypeptides isolated from any source can be modified by methods known in the art. For example, TAF subunits may be phosphorylated or dephosphorylated, glycosylated or deglycosylated, and the like. Especially useful are modifications that alter TAF solubility, membrane transportability, stability, and binding specificity and affinity. Some examples include fatty acid-acylation, proteolysis, and mutations in TBP interaction domains that stabilize binding.

TAFs may also be modified with a label capable of providing a detectable signal, for example, at a heart muscle kinase labeling site, either directly or indirectly. Exemplary labels include radioisotopes, fluorescent compounds, etc. Such labeled TAFs thereof find use, for example, as probes in expression screening assays for proteins that interact with TAF, or in assays for TAF binding to TBP.

Identification of Functionally Important TAF Domains and Binding Partners

The polypeptides, protein complexes, and nucleic acids sequences of the present invention find use in the discovery, design, and development of pharmaceutically useful antifungal agents. The following embodiments of the present invention are directed towards elucidating epitopes and interactions of TAFs and TAF subunits that can be selectively interfered with in a therapeutically beneficial manner.

In one embodiment, the known sequence of a TAF subunit e.g. TAF-145 SEQ ID NO: 1 is used to design synthetic peptides comprising portions of the sequence. These peptides range from about 15 to about 50 amino acids in length. Peptides under 60 amino acids in length may be synthesized routinely using commercially available automated synthesizers. The peptides are then added to a cell-free assembly reaction containing e.g. immobilized TAF complex and soluble radiolabelled TBP. Determining which synthetic peptides inhibit some interact of one or more TAF subunits e.g. with other TAF subunits or with other factors, using routine experimentation, is used to identify different functional domains or epitopes of TAF subunits. For example, a peptide (derived from e.g. TAF-145 SEQ ID NO: 1) that is found using the above-described method to inhibit the binding of TBP to TAF complex is likely to represent a region of TAF- 145 that interacts directly with TBP. In a similar manner, associational domains of different TAF subunits that are involved in interactions among subunits, or between TAF subunits or complexes and other transcriptional components, may be systematically identified. These peptides may themselves constitute useful therapeutic reagents, or may serve as the basis for design and formulation of pharmacologically active compositions.

In another embodiment, important functional domains of TAFs are identified using classical and reverse genetic methods that are well-known in the art. For example, a nested set of deletion mutants can be prepared from any known TAF sequence. In this embodiment, progressively longer amino-terminal and carboxy-terminal deletions (such as those shown for TAF-145 SEQ ID NO: 1 in Example 1) can be engineered in a particular TAF sequence. The resulting set of mutant sequences can be individually expressed in *S. cerevisiae* strains under conditions in which the wild-type version of the TAF is not expressed. By monitoring the function of each mutant, it is possible to identify different regions of each TAF polypeptide that are critical for function i.e. functional domains or epitopes. Based on such studies, using methods that are well-known in the art, it is then possible to selectively introduce defined mutations into different regions of the polypeptide, and perform a similar functional analysis.

An important aspect of the present invention is the selection of functional domains or epitopes of yeast TAF subunits that are, in addition, structurally or functionally distinct from their mammlian homologues. Such domains are particularly useful as targets for antifungal drugs. In the case of TAF-145 SEQ ID NO: 1, the yeast version differs in several important respects from its human homologue, TAF-250 SEQ ID NO: 4. Yeast TAF-145 is approximately half the size of human TAF-250, and the homologous regions display an amino acid similarity and identity of only 58% and 33%, respectively. Yeast TAF-145 lacks the carboxy terminal half of its human counterpart that contains the proposed "Bromo domains" and a region rich in acidic amino acid residues.

Identification of important structural and functional domains of TAFs according to the present invention enables the design and production of useful TAF-derived nucleic acid and peptide-based compounds. For example, fusion proteins may be produced between an important TAF domain and e.g. an enzymatically active fragment of a DNA endonclease. The resulting fusion protein, which can be produced in a fungal cell following introduction into the cell of the hybrid DNA operably linked to an expression vector, finds use in modulating TAF-dependent gene transcription. Other useful TAF fusion partners include sequences useful for immobilization. For example, sequences derived from glutathione-S-transferase (GST) provide a binding site for immobilized glutathione, and sequences that form an epitope recognized by an available monoclonal antibody (e.g. 12CA5 monoclonal antibody) provide a binding site for the immobilized antibody.

In another example, particular serine, threonine, or tyrosine residues in a TAF sequence may be identified as functionally important sites for phosphorylation of TAF. See e.g. methods disclosed in Roberts et al. (1991) Science 253, 1022–1026 and in Wegner et al. (1992) Science 256, 370–373. Phosphorylation of TAF subunits may be involved in modulating the transcription activation activity of Polymerase II transcribed genes. Identification of these residues will enable, first, the radiolabelling of TAF subunits with $\gamma$-$^{32}$P-ATP. Furthermore, if phosphorylation of a particular residue is necessary for transcriptional activity, phosphorylation inhibitors may be designed to block activity.

The nucleic acids encoding TAF may also be used to identify other nuclear factors that interact with TAF. In this embodiment, a yeast cDNA library containing fusion genes of cDNA joined with DNA encoding the activation domain of a transcription factor (e.g. Gal4) is co-transfected with fusion genes encoding a portion of TAF and the DNA binding domain of a transcription factor. Clones encoding TAF binding proteins are able to complement the transcription factor and are identified through transcription of a reporter gene. See, e.g. Fields and Song (1989) *Nature* 340: 245–246 and Chien et al. (1991) *Proc Natl Acad Sci USA* 88: 9578–9582. It is contemplated that these additional binding partners for TAF will provide additional targets for antifungal drug therapy.

Anti-TAF Antibodies

The present invention encompasses antibodies that are specific for TAF complexes or subunits identified as described above. The antibodies may be polyclonal or monoclonal, and may distinguish TAFs from other nuclear proteins, discriminate TAFs from different species, identify associational or other functional domains, and the like. Such antibodies are conveniently made using the methods and compositions disclosed in Harlow and Lane, *Antibodies, A Laboratory Manual*, Cold Spring Harbor Laboratory, 1988, other references cited herein, as well as immunological and hybridoma technologies known to those in the art. Where natural or synthetic TAF-derived peptides are used to induce an TAF-specific immune response, the peptides may be conveniently coupled to an suitable carrier such as KLH and administered in a suitable adjuvant such as Freunds. Preferably, selected peptides are coupled to a lysine core carrier substantially according to the methods of Tam (1988) *Proc Natl Acad Sci USA* 85, 5409–5413. The resulting antibodies may be modified to a monovalent form e.g. Fab, FAB', or FV. Anti-idiotypic antibodies, especially internal imaging anti-idiotypic antibodies, may also be prepared using known methods.

In one embodiment, purified TAF-145 SEQ ID NO: 1 is used to immunize mice, after which their spleens are removed, and splenocytes used to form cell hybrids with myeloma cells and obtain clones of antibody-secreted cells according to techniques that are standard in the art. The resulting monoclonal antibodies are screened using in vitro assays such as those described above for the following activities: binding to TAF-145 SEQ ID NO: 1, inhibiting the incorporation of TAF-145 into multimeric TAF complexes, and inhibiting the interaction between TAF-145 SEQ ID NO: 1 and TBP.

In another embodiment, the entire TAF complex is used as an immunogen as above, and the resulting monoclonal antibodies are screened for their activity in inhibiting the in vitro assembly of any component of the TAF complex.

Anti-TAF antibodies may be used to identify and quantify TAF components, using immunoassays such as ELISA, EMIT, CEDIA, SLIFA, and the like. Anti-TAF antibodies may also be used to block the transcriptional function of TAF by inhibiting formation of complexes between TAF subunits or between assembled TAF complexes and other transcription components, or by immunodepleting cell extracts or transcription reactions of TAF components. In addition, these antibodies can be used to identify, isolate, and purify TAFs from different sources, and to perform subcellular and histochemical localization studies.

High-Throughput Drug Screening

The present invention encompasses the identification of agents useful in modulating fungal gene transcription, particularly the transcription of genes by RNA Polymerase II in a TAF-dependent manner. In a preferred embodiment, a high-throughput screening protocol is used to survey a large number of test compounds for their ability to interfere with TAF-dependent processes.

Test inhibitory compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means.

Useful inhibitory agents are identified with a range of assays employing TAF or TAF-encoding nucleic acids. As examples, protein binding assays, nucleic acid binding assays and gel shift assays are useful approaches. Preferably, TAF complexes or subunits as provided by the present invention may be used in in vitro binding assays with either TBP alone or with a combination or subcombination of TBP and general transcription factors (GTFs).

For example, TAF complexes or subunit may be immobilized on microtiter dishes using methods that are standard in the art. The plates are then exposed to radiolabelled TBP e.g. $^{32}$P-TBP in the absence or presence of candidate compounds. Conversely, TBP may be immobilized, and incubated with radiolabelled TAF in the absence or presence of candidate compounds. Oligonucleotides comprising TBP target sequences may be used in conjunction with TBP and TAF (see Example 2 below.) Postive "hit" compounds are those that inhibit TAF-TBP interaction. In these case, incubation, washing, and radioactivity detection steps can be automated, allowing the screening of a large number of compounds, preferably at least about 1000 compounds per week.

Once a particular test compound has been identified as described above, its activity is then confirmed by adding it to an in vitro transcription reaction, and measuring its effect on TAF-mediated activated transcription (see e.g. Example 1 below.)

It is also contemplated that a useful agent may interfere with the function of TAF but not with TAF-TBP complex assembly. To screen for such compounds, other functional assays are used e.g. in vitro transcription reactions alone.

Finally, a test compound identified as described above is tested for two properties: 1) Its ability to inhibit fungal growth; and 2) Its lack of effect on mammalian transcription. Fungal growth is measured by any method well-known in the art e.g. optical density of a liquid culture, or colony formation on agar. The lack of effect of a test compound on mammalian TAF-TBP interaction is tested by replacing yeast components with an analogous human in vitro transcription system as in e.g. Manley et al. (1980) *Proc.Natl.Acad.Sci.USA* 77:3855–3859.

It will be understood that a compound that interferes with any aspect of TAF assembly or function is a likely candidate for an antifungal drug. Thus, in a manner similar to that described above for TBP-TAF-145 binding paradigm, binding assays can be routinely devised that measure the interaction of two or more TAF subunits with each other, or the interaction of one or more TAF subunits with other necessary transcription factors.

According to the present invention, useful agents may be found within numerous chemical classes, though typically they are organic compounds, and preferably small organic compounds. Small organic compounds have a molecular weight of more than 50 yet less than about 2,500 daltons, preferably less than about 750, more preferably less than about 250 daltons. Exemplary classes include peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxyl terminus, e.g., for the amino group, acylation or alkylation, and for the carboxyl group, esterification or amidification, or the like. Other methods of stabilization may include encapsulation, for example, in liposomes, etc.

Therapeutic Applications

For therapeutic uses e.g. the treatment of fungal infections in mammals, the compositions and agents disclosed herein may be administered by any convenient way, e.g. parenterally, conveniently in a physiologically acceptable carrier, e.g., phosphate buffered saline, saline, deionized water, or the like. Typically, the compositions are added to a retained physiological fluid such as blood or synovial fluid. Alternatively, the compositions may comprise creams, ointments, lotions, or sprays for topical use. Generally, the amount administered will be empirically determined, typically in the range of about 10 to 1000 pg/kg of the recipient. For peptide agents, the concentration of will generally be in the range of about 100 to 500 ug/ml in the dose administered. Other additives may be included, such as stabilizers, bactericides, etc. These additives will be present in conventional amounts.

EXAMPLE 1

Identification of Yeast TAFs

The studies described below were performed to identify and isolate transcriptional activator factors (TAFs) from *S. cerevisiae.*

EXPERIMENTAL PROCEDURES

Selective Depletion of an Essential Coactivator on a GST-yTBP Column

A whole cell extract (WCE) from *S. cerevisiae* strain Y57 was prepared as described (Woontner, M., et al. *Mol. Cell. Biol.* 11, 4555–4560 (1991)) except that the ammonium sulfate pellet was dissolved and dialyzed into Buffer T containing 0.1M potassium acetate. Buffer T is 20 mM HEPES-KOH ph 7.6, 10 mM magnesium acetate, 5 mM EGTA, 5 mM DTT and 20% (v/v) glycerol plus protease inhibitors: 0.5 ug/ml each of leupeptin, pepstatin A, aprotinin, antipain-HC1, chymostatin, bestatin; 2mM benzamidine-HC1 and 0.5 mM PMSF.

The WCE was diluted and chromatographed on a 2.5 ml column containing yeast TBP bound to glutathione S-transferase (yTBP-GST) or, as a control, glutathione S-transferase alone (GST). The yeast GST-yTBP plasmid was constructed by cloning the BamHI fragment from pASYIID (Schmidt, M. et al. Proc. Natl. Acad. Sci. U.S.A. 86, 7785–7789 (1989)) into pGEX-1. GST-yTBP and GST columns were prepared as described (Lin, Y-S. & Green, M. R. Cell 64, 971–981 (1991)).

The WCE was diluted in buffer T (0.1M KOAc) and passed four times over the columns followed by washing with 5 volumes of 0.2M KOAc buffer T. Bound proteins were eluted with buffer T containing 2M KC1 for analytical runs. Eluates and flowthrough fractions were dialyzed into buffer T (0.1M KOAc). Flowthrough fractions (4 ml), peak 2M KC1 eluates (1–2 ml), and an aliquot of unfractionated WCE were collected and dialyzed in parallel.

The transcriptional activating activity of each fraction was measured. Reaction mixtures contained 8 ul of WCE or column flowthrough fractions and 5 ul of eluate fractions and were performed in the presence (+) or the absence (−) of 100 ng of GAL4-VP16 ml of gel. Transcription reactions were performed, and samples processed as described (Woontner, M., et al. Mol. Cell. Biol. 11, 4555–4560 (1991) ). Briefly, reaction mixtures (30 ul) contained 80–120 ug of WCE or GST-yTBP flowthrough fraction in 25 mM HEPES-KOH, pH 7.6, 10 mM magnesium acetate, 2.5 mM EGTA, 2 mM DTT, 8–10% (v/v) glycerol, 90–110 mM potassium acetate, 5 mM phosphocreatine, 1U creatine kinase (Sigma), 10U RNasin, 100 ng of template, approximately 100 ng of GAL4-VP16 fusion, protein where indicated. GAL4-VP16 was prepared as described (Chasman, D. I. et al. Mol. Cell. Biol. 9, 4746–4749 (1989)), except that acetate buffers were used and the protein was further purified by heparin-agarose chromatography.

Purification of the Coactivator

Approximately 2 g of WCE protein was passed four to five times over a 40 ml GST-TBP column equilibrated in buffer T (0.1M KOAc), and the column was washed with 5 column volumes of T (0.2M KOAc). The column was eluted by step gradients of: 40 ml 0.5M KOAc, 40 ml 1.0M KOAc, and 50 ml 2M KCL containing 0.003% NP-40, all in Buffer T. Most of the activity eluted in the 2M KCL fraction. The fractions were dialyzed in buffer T (0.1M KOAc.) containing 0.003% NP-40. Aliquots were removed and analyzed by SDS-PAGE and visualized by Silver staining. Fractions were assayed for transcriptional activity by addition to a GST-yVP16 flowthrough in the presence and absence of GAL4-TBP. The peak activity from six columns (Total WCE Protein load 12 g, 800 ml) were pooled (9.5 mg, 180 ml) and passed over a 3 ml P11 column equilibrated in T (0.1M KOAc). The flowthrough fraction (8.6 mg, 185 ml) was loaded onto a 5 ml Econopak S-cartridge (BioRAD) equilibrated in Buffer A (0.1). Buffer A is 20 mM HEPES-KOH pH 7.6, 2 mM DTT, 1 mM EDTA, 0.003% (v/v) NP-40, 20% (v/v) glycerol and the molarity of potassium acetate indicated in parentheses. The S-column was washed and eluted with a linear gradient of A(0.1) to A(0.5). Peak fractions eluted as a broad peak from 0.2M to 0.35M KOAc, and were identified by transcription assays. The peak S-column fractions (2.1 mg, 36 ml) were dialyzed in buffer A(0. 1) and loaded onto a 1 ml Econopak hydroxylapatite column equilibrated in buffer C (0.1M potassium phosphate pH 7.7, 0.2 mM EDTA, 2 mM DTT, 0.01% (v/v) NP-40, 20% (v/v) glycerol), washed, and eluted with a linear gradient to 0.3M potassium phosphate. Peak fractions eluting between 0.15M and 0.30M were pooled and dialyzed into buffer A (0.1). Approximately 1 mg (14 mls) of protein was recovered following hydroxylapatite chromatography.

To measure transcription activity of the final Hydroxylapatite fraction, the GST-yTBP flowthrough (75 ug of protein) was supplemented with increasing quantities of the hydroxylapatite fraction (approximately 50–500 ng) in the presence (+) or absence (−) of 100 ng GAL4-VP16.

In some cases, the hydroxylapatite fraction (150 uL) was analyzed on a Superose 6 gel filtration column (HR 10/30) in Buffer A (0.3M KOAc).

Co-immunoprecipitation of Coactivator and TBP

A yeast WCE was diluted and adjusted to 0.35M KOAc with buffer T containing 1.0M KOAc, and NP-40 was added to 0.1% (v/v). To pre-clear the extract, 3 ml aliquots (40 mg/ml protein) were incubated for 6 hr with 0.1 ml of washed Protein A-agarose beads. Two micrograms of affinity purified pre-immune or α-TBP antibody (Poon, D. & Weil, P. A. J. Biol. Chem. 268, 15325–15328 (1993)) were added and incubated on ice for 5 hr. Ten microliters Protein A-agarose were added, and the incubation continued for 16 hr with rotation at 40° C. Prior to recovering the immune-complexes by centrifugation, 25 uL of Protein A beads were added as carrier. Beads were then washed four times with 1 ml of buffer T (0.9M KOAC) containing 0.1% NP-40 (v/v). yTAFIIs were eluted by washes of buffer T (2M KC1) plus 0.1% NP-40 (v/v) and 0.1 mg/ml insulin, followed by dialysis into: 20 mM HEPES pH 7.5, 5 mM EGTA, 0.15M KOAc, 10 mM magnesium acetate, 1 mM DTT, 10% glycerol (v/v).

Far Western Blotting

The hydroxylapatite fraction was separated by SDS-PAGE and transferred to Immobilon-P membranes, and blocked in buffer T (0.2M KOAc) containing 0.01% (v/v) NP-40 and 4% BSA for 3 hr at room temperature followed by 2 hr at 40° C. $^{35}$S-labeled yTBP and hTBP and its mutant derivatives (Ha, I. et al. Genes & Dev. 7, 1021–1032 (1993)) were synthesized in rabbit reticulocyte lysate and wheat germ extract, respectively, and were diluted in incubation buffer (buffer T (0.2) plus 0.01% (v/v) NP-40 and 0.5% BSA). Blots were incubated with comparable amounts of labeled proteins estimated by fluorography of a SDS/PAGE gel. The membrane was incubated with probe at 40° C. for 14–18 min, twice in incubation buffer without BSA for 15 min, and rinsed in buffer T (0.2) lacking glycerol for 20 sec. The membrane was air dried, and exposed directly to film for 8–24 hr.

RNA Polymerase III Transcription

RNA polymerase III activity was monitored by run off transcription of the $^{met}$tRNA gene (Santos, T. & Zasloff, M. Cell 23, 699–709 (1981)), and were performed similar to the RNA polymerase II transcription reactions using 300 ng of template except that RNAse T1 treatment was omitted and guanosine was included in the rNTP mixes. A yeast WCE and the GST-yTBP flowthrough were tested for their ability to support transcription of the $^{met}$tRNA gene. The GST-yTBP flowthrough was also supplemented with the GST-yTBP 2M KC1 eluate (5 uL) or the hydroxylapatite fraction (3 uL) as indicated.

Cloning genes encoding TAF proteins

The hydroxylapatite fraction of yTAFIIs was subjected to SDS/PAGE, the polypeptides transferred to nitrocellulose, and the bands excised for microsequence analysis. A peptide with the sequence ATTEPSAEPDEPFIGYLGDVTA SEQ ID NO:5, was obtained from yTAFII90 SEQ ID NO:2. A BLAST search (Altschul, S. F. et al. J. Mol. Biol. 215, 403–410 (1990)) of the database identified yTAFII90 as an unknown open reading frame on yeast chromosome III. yTAFII90 SEQ ID NO:2 was cloned by PCR from genomic DNA using the primers:

5'-AGATACTTGAAAATCTAGAATGTCACAC-3' SEQ ID NO: 6 and

5'-GGTTATACTTATTACATATCACTTCCATGC-3' SEQ ID NO: 7.

The peptides NINHLFTVGQTFPVEEIPGPN SEQ ID NO: 8 and LPVGETHVLGVQDKSPF SEQ ID NO: 9 were obtained from yTAFII145 SEQ ID NO: 1 and the degenerate oligonucleotides 5'-TT(C/T)CCNGTNGA(A/G)GA(A/G) AT-3' SEQ ID NO: 10 and 5'-GTNGGNGA(A/G)ACNCA (C/T) GT-3' SEQ ID NO: 11 were designed and used to screen a yeast genomic library (Rose, M. D. et al. Gene 60, 237–243). Two clones were selected that contained the same 10 kb insert. The open reading frame was identified by sequencing and by its homology to drosophila and human TAFII250. No other extended ORFs were found in the sequence.

Genetic Analysis

A disrupted copy of the yTAFII90 gene was generated by insertion of the HIS 3 gene (Bam HI fragment) into the Bg1 II site (amino acid 489) and Bam HI site (amino acid 628) within the coding region, and a disrupted copy of the yTAFII145 gene was constructed by insertion of the LEU2 gene (blunted Bam HI/Hind III fragment) into the blunted Bg1 II/Cla I sites (amino acid 233 and 645). These fragments were used to transform the strain CY236 to histidine (strain LY1) or leucine (strain YSW57) prototrophy.

RESULTS

Identification of a Yeast Coactivator that Binds TBP

To identify yeast coactivators that bind TBP, protein affinity-chromatography was carried out using *S. cerevisiae* TBP (yTBP) as the immobilized ligand. An *S. cerevisiae* whole cell extract (yWCE) was cliromatographed on a control glutathione S-transferase (GST) or a GST-yTBP column. The flowthrough fraction was tested for its ability to support transcription in the presence or absence of the activator GAL4-VP16. The DNA template used in these experiments contained the yeast cycl promoter and a single GAL4 binding site upstream of the TATA box (FIG. 1, bottom; Kelleher, R. J., Flanagan, P. M. & Kornberg, R. D. Cell 61, 1209–1215 (1990)).

FIG. 1 shows that the flowthrough of the GST column supported both basal (lane 3) and activated (lane 4) transcription. In contrast, the flowthrough of a GST-yTBP column did not support activated transcription (lane 10), whereas basal transcription remained intact (lane 9). Thus, under these chromatographic conditions, yTBP selectively depleted a coactivator from the yWCE.

Addition of the 2M KC1 eluate from the GST-yTBP column restored the ability of the GST-yVP16 flowthrough to respond to GAL4-TBP (lane 14), whereas the eluate of the GST column had no effect (FIG. 1 and data not shown). The 2M KC1 eluate from the GST-yTBP column had no transcriptional activity on its own (lanes 11 and 12), and did not significantly affect activator-independent basal transcription (lane 13). Taken together, these data identify an essential yeast coactivator activity that binds TBP.

Purification of the Coactivator

The coactivator implicated by the protein affinity-chromatography experiments was purified next. The GST-yTBP column was eluted with salt, and the fractions tested for their ability to restore activated transcription to the GST-yTBP flowthrough. The majority of bound protein eluted from the yTBP affinity column at 0.5M potassium acetate, whereasmost of the coactivator activity eluted in the 2M KC1 fraction, which contained only 0.07% of the total protein (data not shown).

Figure 2A:
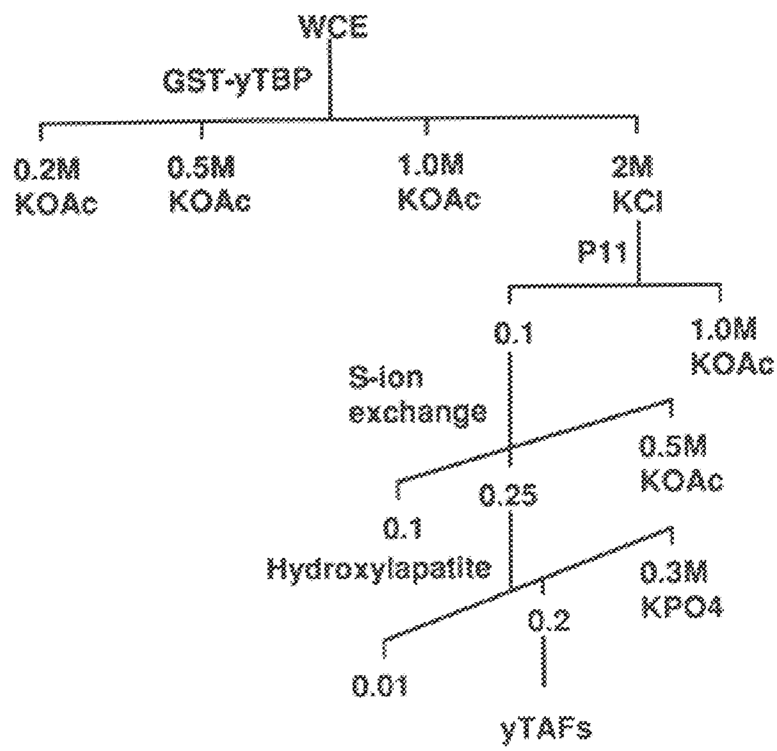
FIG. 2A shows the purification protocol for yeast transactivating factor complex (TAF).
Figure 2B:
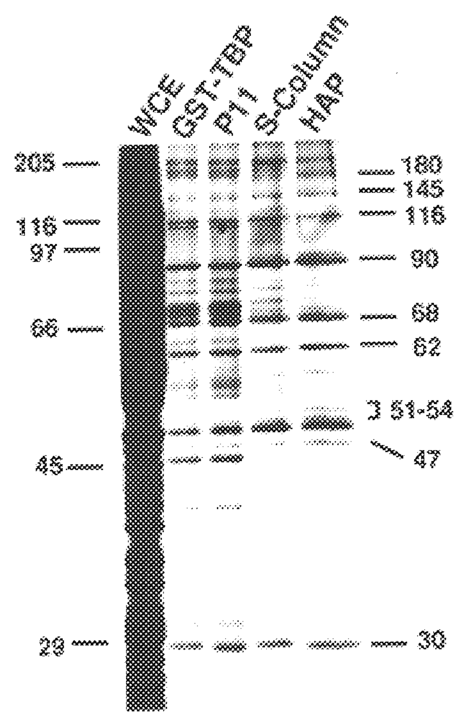
FIG. 2B shows an SDS-polyacrylamide gel profile of the polypeptides present in the fractions shown in FIG. 2A. The migration of molecular mass markers are indicated on the left and the yeast TAF polypeptides are indicated on the right.

The coactivator was further purified from the GST-yTBP 2M KC1 eluate according to the scheme outlined in FIG. 2A. The fractions with maximal coactivator activity from each column were identified by a transcription assay performed in the presence or absence of GAIA-VP16. The polypeptide composition of these peak fractions from each column is shown in FIG. 2B. The final fraction from the hydroxylapatite column contained approximately eleven major polypeptides, ranging from 30–200 kD, and a number of minor peptides. Nine of these polypeptides, (180 kD, 145 kD, 116 kD, 90 kD, 68 kD, 62 kD, 51–54 kD, 47 kD, 47 kD and 30 kD) cofractionated with the transcriptional activity (FIG. 2B and data not shown), and co-eluted on a Superose 6 gel filtration column (see below).

Figure 2C:
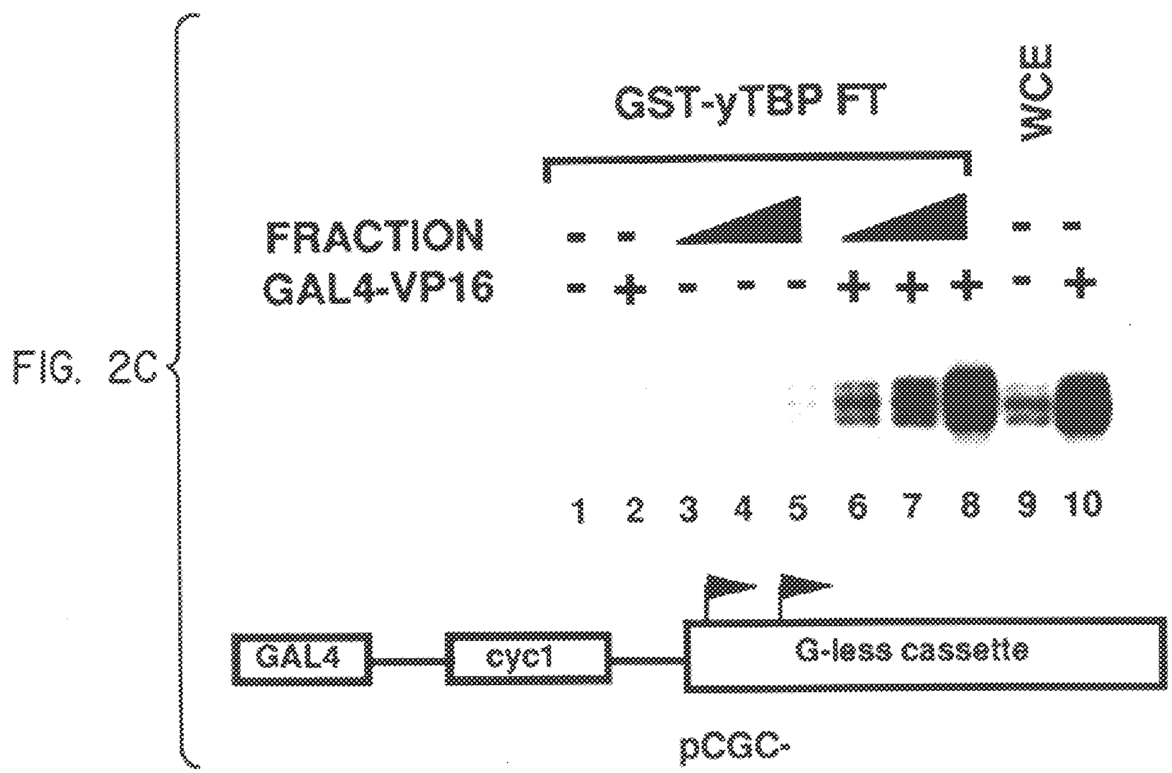
FIG. 2C shows transcription reactions containing increasing amounts of the final hydroxylapatite TAF-containing fraction shown in FIG. 2B.

FIG. 2C shows that addition of the final hydroxylapatite fraction to the GST-VP16 flowthrough fraction restored, in a dose-dependent fashion, the ability of GAL4-TBP to activate transcription (lanes 6–8). In contrast, equivalent amounts of this fraction had not effect on basal transcription activity (lanes 3–5).

Figure 3A:
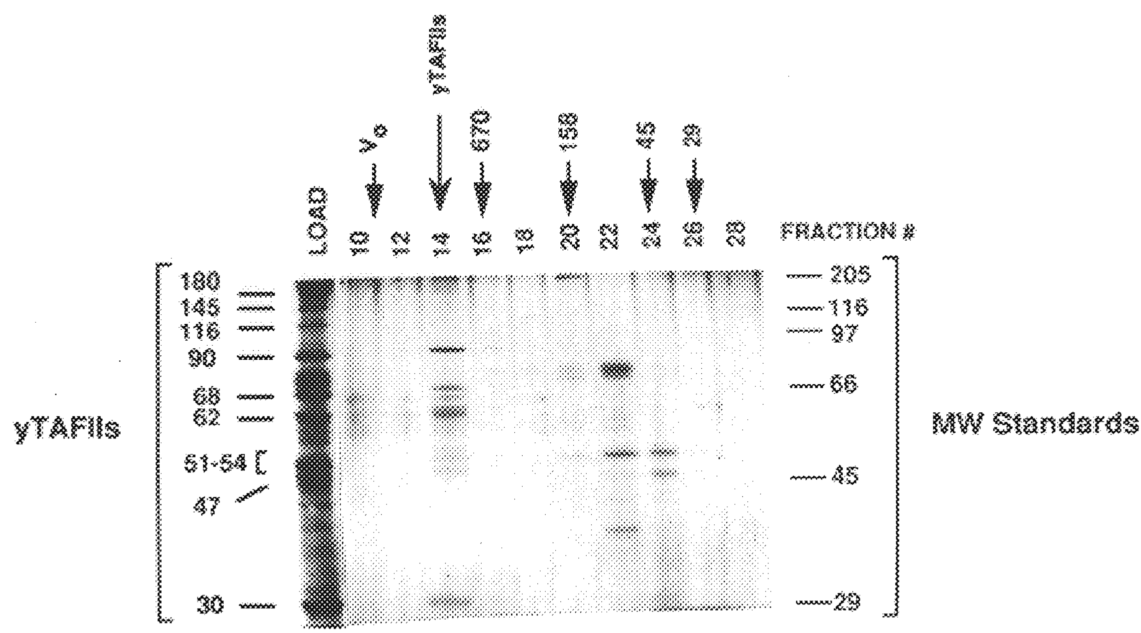
FIG. 3A shows the polypeptide composition of the final hydroxylapatite fraction of FIG. 2B when rechromatographed on a Superose 6 gel filtration column.

The co-elution of these polypeptides over the four chromatographic columns in FIG. 2 suggested that they may be components of a single complex. To confirm this possibility, the final hydroxylapatite fraction was analyzed by gel filtration chromatography. FIG. 3A shows that on a Superose 6 gel filtration column nine of the polypeptides eluted as a complex with a native molecular mass of 800 kD (fraction 14). Two of the eleven major polypeptides contained in the hydroxylapatite fraction, 200 kD and 50 kD, eluted separately in fractions 20 and 22–24, respectively. These two polypeptides also eluted slightly ahead of the complex on the hydroxylapatite column (data not shown). FIG. 3A also reveals a cluster of polypeptides of 51–54 kD that eluted with the complex but were not well visualized in the hydroxylapatite fraction due, at least in part, to masking by the 50 kD contaminant (FIG. 2B). Significantly, this 51–54 kD cluster of polypeptides was also co-immunoprecipitated with an α-TBP antibody (see below) and they are believed to be components of the complex. These combined data indicated that the coactivator is contained within a complex of approximately nine polypeptides, which we refer to as the *S. cerevisiae* TAF (yTAF) complex.

yTAFs Co-immunoprecipitate with TBP

Figure 3B:
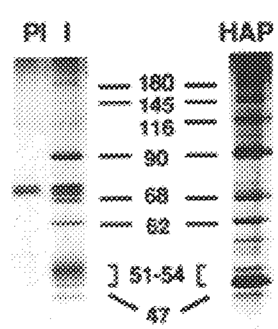
FIG. 3B shows co-immunoprecipitation of yeast TAF polypeptides by an anti-TBP antibody.
Figure 3C:
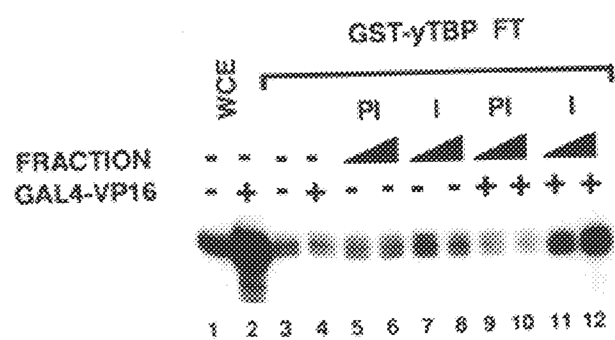
FIG. 3C shows a transcription reaction supplemented with TAF polypeptides immunoprecipitated as in FIG. 3B.

To provide additional evidence that the coactivator bound TBP, co-immunoprecipitation experiments were carried out using an α-TBP antibody. Immunoprecipitation were carried out in a yeast whole cell extract and the immunoprecipitates analyzed for their polypeptide composition by SDS-PAGE and silver staining (FIG. 3B), and for their ability to restore activated transcription to the GST-yTBP flowthrough (FIG. 3C). Strikingly, eight of the nine major polypeptides present in the chromatographically purified yTAF complex were clearly co-immunoprecipitated by the α-TBP antibody and not by the control pre-immune serum (FIG. 3B). The sole exception was yTAF116, which could result from dissociation during washing of the immune-complexes. Significantly, the immunoprecipitate contained the cluster of 51–54 kD polypeptides discussed above. The following experiment was carried out to determine whether the immuniprecipitate contained the coactivator activity. Immune-complexes immobilized on protein A agarose beads were washed with 2M KC1, which released the TBP-associated polypeptides but not TBP. FIG. 3C shows that the 2M KC1 wash of the immune-complexes partially restored activated transcription to the GST-yTBP flowthrough (lanes 11–12) without affecting the basal level (lanes 7–8). Thus, an activity required for activated transcription was co-immunoprecipitated with TBP. The reduced coactivator activity of the immune-complex eluate, compared to the hydroxylapatite fraction (compare FIGS. 2C and 3C), is consistent with the 5–8 fold lower concentration of yTAFs in the immune-complex eluate (see FIG. 3B and legend).

The C-Terminal Domain of TBP Binds to yTAF145

Figure 4A:
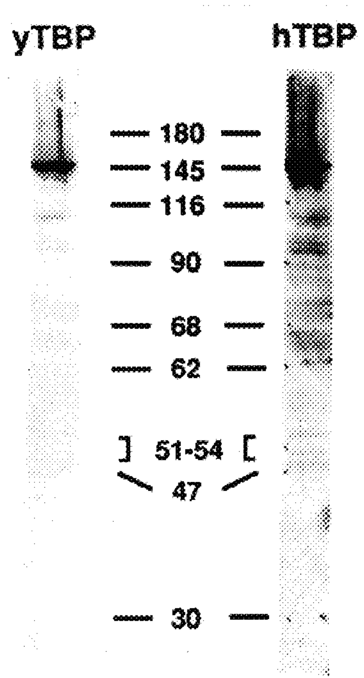
FIG. 4A shows a protein blot in which TAF polypeptides were resolved by SDS-gel electrophoresis, transferred to nitrocellulose, and incubated with $^{35}$S-labelled yeast (y) or human (h) TBP.
Figure 4B:
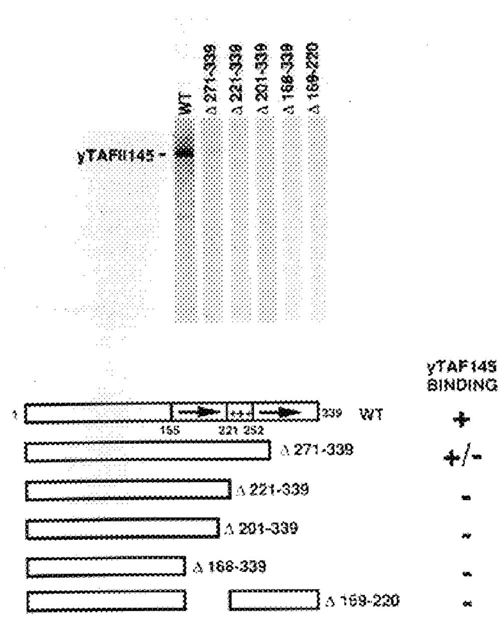
FIG. 4B shows a similar protein blot as in FIG. 4A, except that the indicated C-terminal deletion mutants of TAF-145 were utilized in parallel with full-length TAF-145.

The results from the protein affinity-chromatography and co-immunoprecipitation experiments described above strongly suggested that one or more subunits of the yTAF complex bound TBP directly. To identify this subunit, the yTAF complex was examined for TBP binding using an immobilized protein blotting ("Far Western") assay. The hydroxylapatite fraction was fractionated by SDS-PAGE, the polypeptides transferred to nitrocellulose, and the membrane probed with $^{35}$S-labeled yTBP. FIG. 4 shows that a single subunit of the yTAF complex, the 145 kD polypeptide (yTAF145)SEQ ID NO: 1, was bound by yTBP. FIG. 4 shows that $^{35}$S-labeled human TBP also bound to yTAF145.

The fact that both human and *S. cerevisiae* TBP bind to yTAF145 SEQ ID NO: 1 implies that the interaction occurs through the C-terminal domain of TBP, which is conserved between human and *S. cerevisiae* TBP. To map the region of TBP required for binding to yTAF145, we analyzed several previously characterized human TBP mutants (Ha, I. et al. Genes & Dev. 7, 1021–1032 (1993)). Deletion of most of the second direct repeat led to a significant reduction in the interaction between TBP and yTAF145 (FIG. 4B; lane 2), and deletion of another 50 amino acids totally abolished binding (lane 3). Significantly, this same region was shown to bind hTAF250. A mutant lacking most of the second direct repeat, but containing the first direct repeat and the basic region of TBP also failed to bind yTAF145 (169–220; lane 6). Therefore, it appears that TBP interacts with yTAF145 through both direct repeats, consistent with the saddle structure of TBP (Nikolov, D. B. et al. Nature 360 40–46 (1992); Chasman, D. I. et al. Proc. Natl. Acad. Sci. USA 90, 8174–8178 (1993)).

yTAFs are Not Required for Transcription by RNA Polymerase III

In higher eukaryotes, each of the three RNA polymerases contains an essential transcription factor composed of TBP and multiple TAFs. Furthermore, the TAFs involved in transcription by RNA polymerase II, TAFs, are distinct from those involved in transcription by the other two RNA polymerases (reviewed in Hernandez, N. Genes & Dev. 7, 1291–1308 (1993)). In yeast, TBP is also required for transcription by all three RNA polymerases (Cormack, B. P. & Struhl, K. Cell 69, 685–696 (1992); Schultz, M. C., Reeder, R. H. & Hahn, S. Cell 69, 697–702 (1992).

Figure 5:
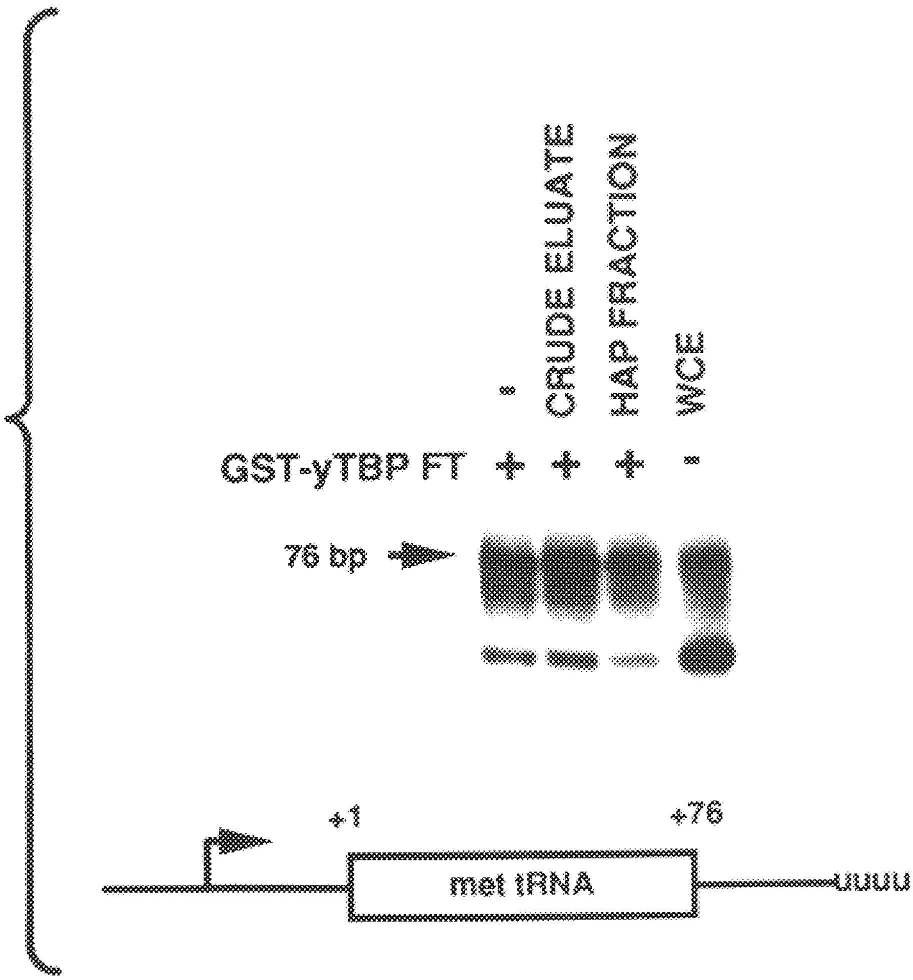
FIG. 5 shows transcription reactions programmed by the RNA polymerase III template shown at the bottom of the figure. The reactions were carried out by WCE and indicated column fractions as in FIGS. 1 and 2C.

The experiments described above demonstrate that a GST-yTBP column depleted a *S. cerevisiae* WCE of TAFs with coactivator activity. The ability of the GST-yTBP flowthrough to support RNA polymerase III-directed transcription was tested to determine whether these TAFs were required for transcription by RNA polymerase III. FIG. 5 shows that the GST-yTBP flowthrough efficiently supported RNA polymerase III transcription, and that this activity was not increased by addition of either the GST-yTBP eluate, or the purified yTAF complex. These combined data demonstrate that the GST-yTBP column selectively depleted a factor required for transcriptional activation by RNA polymerase II. It is, of course, possible that under different chromatographic conditions the GST-yTBP column could also deplete TAFs involved in RNA polymerase III transcription.

Yeast Homologues of Higher Eukaryotic TAFs

The yTAF complex was purified as described above and the polypeptides isolated for microsequence analysis. A protein database search of a tryptic peptide derived from yTAF90 SEQ ID NO: 2 revealed that it was present within a previously sequenced gene on yeast chromosome m (Oliver, S. G. et al. Nature 357, 38–46 (1992)). The amino acid sequence of yTAF90 contains WD40, or β-transducin repeats (van der Voorn, L. & Ploegh, H. L. FEBS Lett. 307, 131–134 (1992)). Drosophila TAF80 (dTAF80) SEQ ID NO: 3 also contains these motifs, and yTAF90 SEQ ID NO: 2 and dTAF80 are somewhat homologous (FIG. 6A); yTAF90 has 31% identity and 53% similarity with dTAF80, a degree of homology equivalent no greater than that between human and yeast TFIIB, which are analogous but not interchangeable (Pinto, I., Ware, D. E. & Hampsey, M. Cell 68, 977–988 (1992)). The similar size and sequence indicates that yTAF90 is the yeast homologue of dTAF80.

Two peptide sequences were obtained from yTAF 145 SEQ ID NO: 1, degenerate oligonucleotides were designed and used to screen a plasmid yeast genomic DNA library. DNA sequence analysis of positive clones revealed an open reading frame of 1066 amino acids, with a calculated molecular weight of 120,685 kDa. This value is somewhat smaller that the molecular weight estimated by polyacrylamide gel electrophoresis (145 kDa), possibly due to the highly charged nature of yTAF145. The N-terminus of yTAF145 is highly acidic (pI 3.3), while the C-terminus is rich in basic residues (pI 9.3). A data base search of the sequence revealed that it has some homology to both human (FIG. 6B) and drosophila (data not shown) TAF250.

FIG. 6B (bottom) highlights regions of similarity and difference between yTAF145 and hTAF250. Both contain a highly acidic N-terminus rich in serine, homology to bacterial sigma factors, and homology to high mobility group proteins. The C-terminal portion of human and drosophila TAF250 contain "Bromo" domains and an acidic region, which have been proposed to provide a transcription related function (Hisatake, K. et al. *Nature* 362, 179–181 (1993); Ruppert, S., Wang, E. H. & Tjian, R. *Nature* (London) 362, 175–179 (1993); Kokubo, T., et al. *Genes & Dev*. 7, 1033–1046 (1993)). Significantly, this C-Terminal region is absent in yTAF145, indicating an important difference between the yeast and human TAFs.

The Genes Encoding yTAF90 and yTAF145 are Essential

The following procedure was performed to determine whether the genes encoding yTAF90 or yTAF145 are required for cell viability by genetic analysis of strains bearing a disrupted allele of these genes. Constructs containing disrupted copies of yTAF90 and yTAF145 were assembled and used to make diploid yeast strains containing one wildtype and one mutant copy of either gene (FIG. 6, panels C And D, top). The disruptions were confirmed by Southern blotting (FIG. 6, panels C and D, left). These strains were sporulated and their tetrads dissected. The auxotrophic markers for each segregated 2:2 (FIG. 6, panels C and D, bottom right), and in no case did a spore bearing the disruption marker grow, indicating that these genes are essential for cell viability.

DISCUSSION

Identification of fungal coactivators is important for establishing bioassays for the discovery of novel anti-fungal therapeutics. To date, the most well characterized coactivators are the TAFs of the higher eukaryotic TFIID complex (reviewed in Pugh, B. F. & Tjian, R., *J. Biol. Chem.*, 267:679–682 (1992); Sharp, P. A., *Cell*, 68:819–821 (1992); Hernandez, N., *Genes & Dev.*, 7:1291–1308 (1993)). A novel yeast complex has been identified that shares several similarities with higher eukaryotic TFIID, including: (1) both are large multisubunit complexes that contain a single subunit that binds TBP directly; (4) both complexes appear to be specific for RNA polymerase II transcripton; (5) two subunits of the yeast complex, yTAF90 and yTAF145, are the apparent homologues of known subunits of higher eukaryotic TFIID.

Figure 6E:
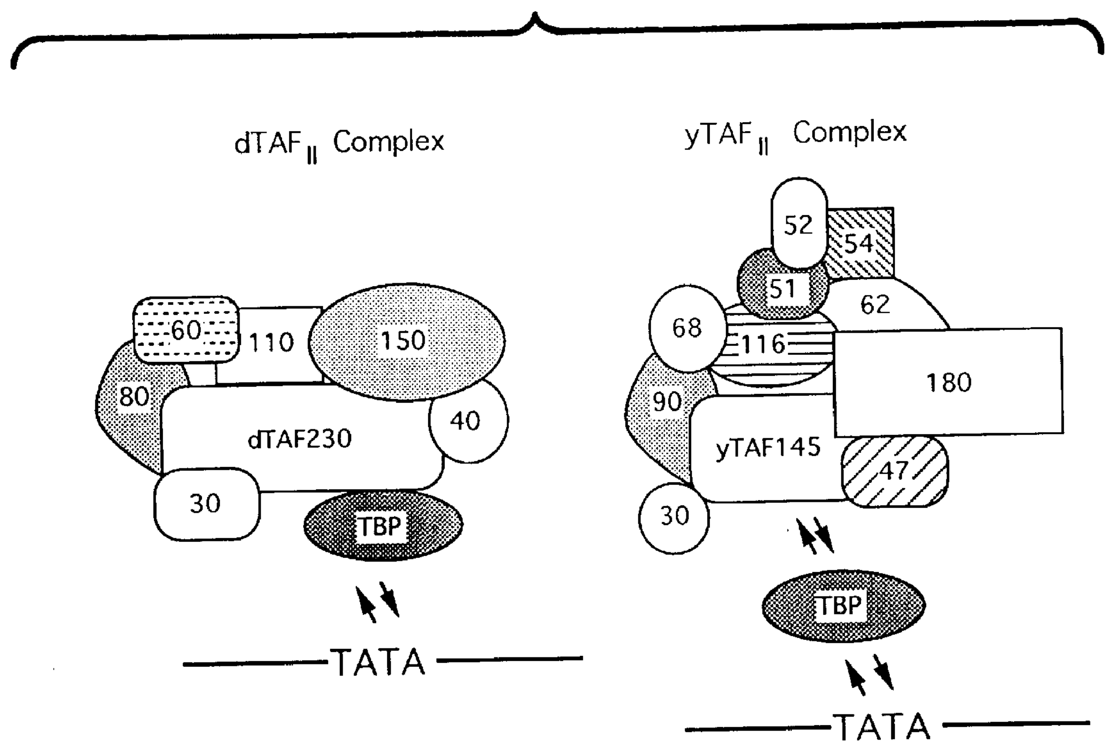
FIG. 6E shows a schematic representation of TAF-containing protein complexes from Drosophila (left) and Saccharomyces (right.)

Differences between TFIID isolated from higher eukaryotes and the yTAF complex described here are exemplified best by the fact that TBP is an integral component of TFIID but is absent from the purified yTAF complex. This apparent disparity is believed to reflect only a difference in the affinity of TBP for the two complexes (FIG. 6E). In higher eukaryotic TFIID, TBP interacts with hTAF25023-27 whereas in the yTAF complex it is the homologous yTAF145 with which TBP interacts (FIG. 4). Presumably, the relatively weak affinity of TBP for yTAF145 has made it previously difficult to identify yeast TAFs.

The weak interaction between yTBP and the yTAF complex demonstrates the possibility for therpeutic intervention. For example, some natural protein negative regulators of transcription interact directly with TBP to prevent either DNA binding (Auble, D. T. & Hahn, S., *Genes & Dev.*, 7:844–856 (1993)), or the interaction of TBP with other GTFs Inostraoza, J. A. et al., *Cell*, 70:477–489 (1992); Meisterernst, M. & Roeder, R. G., *Cell*, 67:557–567 (1991); Meisterernst, M. et al., *Cell*, 66:981–993 (1991)). By analogy, it is conceivable that an antifungal drug could be developed that binds to free yTAF and blocks its interaction with yTBP or that binds to yTBP and blocks its interaction with the yTAF complex. The relatively weak interaction between TBP and the yTAF complex may facilitate disruption of TAF function.

Other Yeast TBP-Binding Proteins

It is important that the yTAF complex disclosed here is distinct from previously identified yeast transcription factors. Genetic and biochemical approaches have identified four factors that interact with yeast TBP (Pinto, I., Ware, D. E. & Hampsey, M., *Cell*, 68:977–988 (1992); Colbert, T. & Hahn, S., *Genes & Dev.*, 6:1940–1949(1992); Eisenmann, D. M. et al., *Genes & Dev.*, 61319–1331(1992); Lopez-de-Leon et al., *Cell*, 71:211–220; Kassavetis, G. A. et al., *Cell*, 71:1055–1064 (1992); Koleske, A. J. et al., *Cell*, 69:883–894 (1992); Poon, D. & Weil, P. A., *J. Biol. Chem.*, 268:15325–15328 (1993)). Two of these factors, the essential RNA polymerase II transcription factor TFIIB (SUA7), and the essential RNA polymerase III transcription factor BRF1/PCF4/TDS4, are unrelated to the yTAF complex based upon transcriptional assays (FIGS. 1, 2C and 5) and microsequence analysis (data not shown).

The yeast protein, SPT3 interacts with TBP on the basis of genetic and biochemical experiments. However, unlike the coactivator activity reported here, SPT3 is not selectively required for activated transcription (Eisenmann, D. M. et al., *Genes & Dev.*, 6:1319–1331 (1992)). Furthermore, immunoblotting experiments indicate that the purified yTAF complex does not contain SPT3.

Recently, a yeast multisubunit complex has been identified that contains RNA polymerase II and a minimum of twelve other subunits (Thompson, C. M. et al., *Cell,* 73:1361–1375 (1993); Kim, Y. -J., et al., *Cell*, 77:599–608 (1994)). This holoenzyme complex contains a group of polypeptides (SRB2, 4, 5 and 6) that had been previously identified as dominant mutations that suppress certain RNA polymerase II C-terminal domain deletion mutants. One of these proteins, SRB2, appears to interact with TBP (Koleske, A. J. et al., *Cell*, 69:883–894 (1992)). Unlike the yTAFs disclosed here, the SRB proteins are necessary for both basal and activated transcription (Koleske, A. J. et al., *Cell*, 69:883–894 (1992); Thompson, C. M. et al., *Cell*, 73:1361–1375 (1993)). Furthermore, immunoblotting experiments indicate that SRB2, SRB4, SRB5, and SRB6 are not present in the purified yTAF complex.

A recent study (Verrijzer, C. P. et al. Science 264, 933–941 (1994)) reported that a cloned Drosophila TAF, dTAF150, bears significant homology to the product of the yeast TSM-1 gene. This study also demonstrated that the TSM-1 protein can bind purified TBP(Verrijzer, C. P. et al., *Science*, 264:933–941 (1994)). However, microsequence analysis indicates that TSM-1 and the yTAF complex disclosed here are distinct entities. Furthermore, we find that TBP binds to only one subunit of the yTAF complex, yTAF145. Consistent with our results in yeast, immunopurified human TFIID appears to lack TAF150 (Hisatake, K. et al., *Nature*, 362:179–181 (1993); Zhou, Q., Boyer, T. G. & Berk, A. J., *Genes & Dev.*, 7:180–187 (1993)) and the presence of TAF150 in drosophila TFIID is variable (Kokubo, T., et al., *Genes & Dev.*, 7:1033–1046 (1993)). Thus, whether or not TSM-1 is a TAF, and the role of TSM-1 in transcription, are issues that remain to be clarified.

Other Yeast Coactivators

Several laboratories have identified yeast coactivator activities (Ha, I. et al., *Genes & Dev.*, 7:1021–1032 (1993); Koleske, A. J. & Young, R. A., *Nature*, 368:466–469 (1994); S. L. et al., *Cell*, 70:251–265 (1992)) which could be the same or different from yTAFs: some human coactivators, such as USA (Meisterernst, M. & Roeder, R. G., *Cell*, 67:557–567 (1991); Meisterernst, M. et al., *Cell*, 66:981–993 (1991) and ACF (Merino, A. et al., *Nature*, 365:227–232 (1993)), are clearly distinct from the known TAFs. The RNA polymerase holoenzyme complex described above was recently shown to direct activator mediated transcription when supplemented with purified yeast GTFs (Kim, Y. -J., et al., *Cell*, 77:599–608 (1994)), and recent studies have shown that this holoenzyme is indistinguishable from a previously biochemically defined mediator fraction (Kim, Y. -J., et al., *Cell*, 77:599–608 (1994)). Genetic studies have led to the identification of a putative coactivator, ADA242. However, yTAF90 and yTAF145 are essential, whereas ADA2 is not. Furthermore, there is no evidence that ADA2 interacts with TBP.

Yeast Contains Multiple TAF Complexes

TBP is a component of the yeast RNA polymerase III transcription factor, TFIIIB (reviewed in Hernandez, N., *Genes & Dev.*, 7:1291–1308 (1993)). Recently, Poon, D. & Weil, P. A., *J. Biol. Chem.*, 268:15325–15328 (1993) have identified a yeast TBP-containing complex required for transcription by RNA polymerase III. This complex contains eight major subunits, including a 70 kD polypeptide that is BRF1/PCR4/TDS4, a known component of TFIIIB. These observations strongly suggest that the complex identified by Poon and Weil is, or is closely related to, TFIIIB.

While it is possible that there are polypeptides in common, several observations indicate that the yTAF complex identified in this study is distinct from the complex described by Poon and Weil. First, the GST-yTBP column failed to deplete an extract of its ability to support transcription by RNA polymerase III, and, conversely, addition of the purified yTAF complex to the GST-yTBP flowthrough did not enhance transcription by RNA polymerase III (FIG. 5). Second, microsequence analysis of yTAF68 confirms that it is not BRF1/PCF4/TDS4 (our unpublished data). Thus, these combined data indicate that yeast contain at least two TBP-binding complexes, required for transcription by RNA polymerase III, and RNA polymerase II (disclosed here).

The identification and cloning of yTAFs provides the opportunity to develop novel antifungal agents using biochemical and genetic screening approaches. For example, the discovery that yTAF90 SEQ ID NO: 3 and yTAF145 SEQ ID NO: 1 are essential for growth and viability of yeast is of particular interest because it proves that drugs blocking the function of either of these proteins will block the growth of fungi. It provides the necessary tools to establish in vitro and cell-based screens for therapeutics.

EXAMPLE 2

High-throughput Screening of Anti-TAF compounds

Corning ELISA strip wells (8 wells per strip) are coated with avidin (1.0 ug per well) by incubating avidin (200 ul of a 5 ug/ml stock) in coupling buffer (per liter: 1.6 g $Na_2CO_3$, 2.9 g, $NaHCO_3$, 0.9 g $NaN_3$) on the well for 12 h at 4° C. The buffer is decanted, and nonspecific binding sites on the wells are blocked with 1% skim milk in phosphate-buffered saline (PBS) for 1 h at 37° C. Blocking buffer is discarded, and a yeast Pol II promoter-containing oligonucleotide (1 pmol/well) is added to the wells and incubated for 30 min at room temperature. The oligonucleotide is double-stranded and contains a biotin tag on the sense strand.

The oligonucleotide-containing solution is then removed, and the wells are washed with 1% milk in PBS. Yeast TBP is mixed with partially purified TAF that had been metabolically labelled with $^{35}$S-methionine or purified TAF-145 similarly labelled, all in HEG buffer (0.1M KC1, 25 mM HEPES pH 7.9, 0.5 mM EDTA, 20% glycerol, 0.01% LDAO, 0.1M AEBSF, 0.1M Na metabisulfite, 10 mM β-mercaptoethanol) plus 200 ug/ml bovine serum albumin (BSA).

The protein mixture is then added to the prepared wells and incubated for 30 min at room temperature. Samples are then removed, and the wells are washed three times with the PBS/milk solution. Wells are separated and put into scintillation vials, scintillation cocktail is added, and samples are counted in a liquid scintillation counter.

Binding of yeast TAF to the wells is found to be dependent on the presence of TBP, bound in turn to the Pol II promoter-containing oligonucleotide. Small molecules, whether purified or present in natural or synthetic mixtures, are introduced into the assay at concentrations ranging from about 20 to about 200 $\mu$M, and appropriate solvent controls are also performed. Compounds that inhibit binding of TAF by more than about 30% are identified, and the inhibitory activity purified if not already available in pure form. Compounds identified as described above are then tested for their ability to inhibit TBP-dependent transcription in a mammalian cell-free system. Alternatively, human TBP is used in place of yeast TBP in the above-described assay for TAF binding to TBP. Thus, a subset of active compounds are identified that selectively interfere with yeast TAF function i.e. are fungal-specific.

EXAMPLE 3

Treatment of Fungal Infections

A compound identified by the methods described in Example 2 as possessing anti-yeast TAF activity is titrated for its fungal growth-inhibiting properties. That is, the concentration range in which the compound effectively suppresses the growth of *Candida albicans* is measured using methods that are standard in the art. The toxicity of the compound for mammalian cells over the identical concentration range is then tested using standard procedures.

A pharmaceutical formulation is prepared in sterile saline containing the above compound in a concentration effective to prevent growth of Candida organisms without affecting the viability or function of mammalian cells i.e. at a concentration at which the compound exhibits minimal or no toxicity, or toxicity at a level generally accepted in the art. The above formulation is administered using an intravenous, intramuscular, or subcutaneous route to treat candidiasis in a mammalian animal.

What is claimed is:

1. An isolated polypeptide having the sequence set forth as SEQ ID NO:1.

2. An isolated polypeptide comprising a fragment of the polypeptide having the sequence set forth as SEQ ID NO:1, which isolated polypeptide inhibits the interaction between said polypeptide having the sequence set forth as SEQ ID NO:1 and TATA-box Binding Protein (TBP).

3. A purified complex isolated from a fungus, said complex comprising a plurality of TBP-associated factors (TAFs), said TAFs having molecular masses of 180 kDa, 145 kDa, 116 kDa, 90 kDa, 68 kDa, 51–54 kDa, 47 kDa, and 30 kDa, respectively, and said complex activating fungal RNA Polymerase II gene transcription of said fungus by associating with TBP, wherein said TAF having a molecular mass of 145 kDa has the sequence set forth as SEQ ID NO:1.

4. The complex of claim 3, wherein said complex is isolated from a fungal species selected from the group consisting of *Saccharomyces cerevisiae, Candida albicans,*

*Histoplasma capsulatum, Coccidioides immitis, Blastomyces dermatitidis, Cryptococcus neoformans*, and *Aspergillus fumigatus*.

5. A purified complex isolated from a yeast, said complex comprising a plurality of TAFs, said TAFs having molecular masses of 180 kDa, 145 kDa, 116 kDa, 90 kDa, 68 kDa, 51–54 kDa, 47 kDa, and 30 kDa, respectively, and said complex having the ability, in conjunction with an upstream transcriptional activator protein, to co-activate yeast RNA Polymerase II gene transcription of said yeast by associating with TBP.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 1066 amino acids
( B ) TYPE: amino acid
( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
( A ) ORGANISM: S. cerevisiae ( v i i ) IMMEDIATE SOURCE:
( B ) CLONE: TAF-145

( x i ) SEQUENCE DESCRIPTION: SEQ ID NO:1:

```
Met Val Lys Gln Gln Gly Ser Gly Lys Thr Asn Leu Ala Asn Glu Asp
1               5                   10                  15

Glu Ala Tyr Glu Ala Ile Phe Gly Gly Glu Phe Gly Ser Leu Glu Ile
            20                  25                  30

Gly Ser Tyr Ile Gly Gly Asp Glu Gly Ala Asn Ser Lys Asp Tyr Thr
        35                  40                  45

Glu His Leu Pro Asp Ala Val Asp Phe Glu Asp Glu Asp Glu Leu Ala
    50                  55                  60

Asp Asp Asp Asp Asp Leu Pro Glu Glu Ser Asp Ala Asn Leu His Pro
65                  70                  75                  80

Ala Met Met Thr Met Gly Ala Tyr Asp Asp Val Asn Glu Asn Gly Ala
                85                  90                  95

Val Leu Gly Ile Asp Ser Asn Ser Leu Asn Met Gln Leu Pro Glu Ile
            100                 105                 110

Asn Gly Asp Leu Ser Gln Gln Phe Ile Leu Glu Asp Asp Gly Gly Thr
        115                 120                 125

Pro Ala Thr Ser Asn Ala Leu Phe Met Gly Met Asp Ala Asn Glu Ile
```

-continued 130 135 140

His Leu Ala Thr Glu Thr Gly Val Leu Asp Gly Ser Gly Ala Asn Glu
145 150 155 160

Ile Gly His Ser Gln Leu Ser Ile Gly Gly Val Asn Gly Asn Asp Met
165 170 175

Ser Ile Asn Gly Gly Phe Ile Met Glu Pro Asp Met Ser Asp Gly Lys
180 185 190

His Lys Lys Ala Thr Lys Leu Asp Leu Ile Asn His Glu Lys Tyr Leu
195 200 205

Leu Lys Lys Tyr Phe Pro Asp Phe Glu Lys Gly Lys Ile Leu Lys Trp
210 215 220

Asn Lys Leu Ile Tyr Arg Arg Ser Val Pro Tyr His Trp His Ser Glu
225 230 235 240

Ile Ser Arg Val Lys Lys Pro Phe Met Pro Leu Asn Leu Lys Phe Lys
245 250 255

Val Gln Gln Asp Asp Lys Arg Leu Phe Asn Ser Arg Thr Ile Ser Tyr
260 265 270

Val Ala Pro Ile Tyr Gln Gly Lys Asn Asn Leu Leu Gln Ser Asn Ser
275 280 285

Ser Ala Ser Arg Arg Gly Leu Ile His Val Ser Ile Asp Glu Leu Phe
290 295 300

Pro Ile Lys Glu Gln Gln Lys Lys Arg Lys Ile Ile His Asp Glu Lys
305 310 315 320

Thr Ile Ser Glu Asp Leu Leu Ile Ala Thr Asp Asp Trp Asp Gln Glu
325 330 335

Lys Ile Ile Asn Gln Gly Thr Ser Ser Thr Ala Thr Leu Ala Asp Ser
340 345 350

Ser Met Thr Pro Asn Leu Lys Phe Ser Gly Gly Tyr Lys Leu Lys Ser
355 360 365

Leu Ile Glu Asp Val Ala Glu Asp Trp Gln Trp Asp Glu Asp Met Ile
370 375 380

Ile Asp Ala Lys Leu Lys Glu Ser Lys His Ala Glu Leu Asn Met Asn
385 390 395 400

Asp Glu Lys Leu Leu Leu Met Ile Glu Lys Thr Asn Asn Leu Ala Gln
405 410 415

Gln Lys Gln Gln Leu Asp Ser Ser Asn Leu Ile Leu Pro Leu Asn Glu
420 425 430

Thr Ile Leu Gln Gln Lys Phe Asn Leu Ser Asn Asp Asp Lys Tyr Gln
435 440 445

Ile Leu Lys Lys Thr His Gln Thr Lys Val Arg Ser Thr Ile Ser Asn
450 455 460

Leu Asn Ile Gln His Ser Gln Pro Ala Ile Asn Leu Gln Ser Pro Phe
465 470 475 480

Tyr Lys Val Ala Val Pro Arg Tyr Gln Leu Arg His Phe His Arg Glu
485 490 495

Asn Phe Gly Ser His Ile Arg Pro Gly Thr Lys Ile Val Phe Ser Lys
500 505 510

Leu Lys Ala Arg Lys Arg Lys Arg Asp Lys Gly Lys Asp Val Lys Glu
515 520 525

Ser Phe Ser Thr Ser Gln Asp Leu Thr Ile Gly Asp Thr Ala Pro Val
530 535 540

Tyr Leu Met Glu Tyr Ser Glu Gln Thr Pro Val Ala Leu Ser Lys Arg
545 550 555 560

-continued

Gly Met Ala Asn Lys Leu Ile Asn Tyr Tyr Arg Lys Ala Asn Glu Gln
565 570 575

Asp Thr Leu Arg Pro Lys Leu Pro Val Gly Glu Thr His Val Leu Gly
580 585 590

Val Gln Asp Lys Ser Pro Phe Trp Asn Phe Gly Phe Val Glu Pro Gly
595 600 605

His Ile Val Pro Thr Leu Tyr Asn Asn Met Ile Arg Ala Pro Val Phe
610 615 620

Lys His Asp Ile Ser Gly Thr Asp Phe Leu Leu Thr Lys Ser Ser Gly
625 630 635 640

Phe Gly Ile Ser Asn Arg Phe Tyr Leu Arg Asn Ile Asn His Leu Phe
645 650 655

Thr Val Gly Gln Thr Phe Pro Val Glu Glu Ile Pro Gly Pro Asn Ser
660 665 670

Arg Lys Val Thr Ser Met Lys Ala Thr Arg Leu Lys Met Ile Ile Tyr
675 680 685

Arg Ile Leu Asn His Asn His Ser Lys Ala Ile Ser Ile Asp Pro Ile
690 695 700

Ala Lys His Phe Pro Asp Gln Asp Tyr Gly Gln Asn Arg Gln Lys Val
705 710 715 720

Lys Glu Phe Met Lys Tyr Gln Arg Asp Gly Pro Glu Lys Gly Leu Trp
725 730 735

Arg Leu Lys Asp Asp Glu Lys Leu Leu Asp Asn Glu Ala Val Lys Ser
740 745 750

Leu Ile Thr Pro Glu Gln Ile Ser Gln Val Glu Ser Met Ser Gln Gly
755 760 765

Leu Gln Phe Gln Glu Asp Asn Glu Ala Tyr Asn Phe Asp Ser Lys Leu
770 775 780

Lys Ser Leu Glu Glu Asn Leu Leu Pro Trp Asn Ile Thr Lys Asn Phe
785 790 795 800

Ile Asn Ser Thr Gln Met Arg Ala Met Ile Gln Ile His Gly Val Gly
805 810 815

Asp Pro Thr Gly Cys Gly Glu Gly Phe Ser Phe Leu Lys Thr Ser Met
820 825 830

Lys Gly Gly Phe Val Lys Ser Gly Ser Pro Ser Ser Asn Asn Asn Ser
835 840 845

Ser Asn Lys Lys Gly Thr Asn Thr His Ser Tyr Asn Val Ala Gln Gln
850 855 860

Gln Lys Ala Tyr Asp Glu Glu Ile Ala Lys Thr Trp Tyr Thr His Thr
865 870 875 880

Lys Ser Leu Ser Ile Ser Asn Pro Phe Glu Glu Met Thr Asn Pro Asp
885 890 895

Glu Ile Asn Gln Thr Asn Lys His Val Lys Thr Asp Arg Asp Asp Lys
900 905 910

Lys Ile Leu Lys Ile Val Arg Lys Lys Arg Asp Glu Asn Gly Ile Ile
915 920 925

Gln Arg Gln Thr Ile Phe Ile Arg Asp Pro Arg Val Ile Gln Gly Tyr
930 935 940

Ile Lys Ile Lys Glu Gln Asp Lys Glu Asp Val Asn Lys Leu Leu Glu
945 950 955 960

Glu Asp Thr Ser Lys Ile Asn Asn Leu Glu Glu Leu Glu Lys Gln Lys
965 970 975

Lys Leu Leu Gln Leu Glu Leu Ala Asn Leu Glu Lys Ser Gln Gln Arg
980 985 990

```
Arg Ala Ala Arg Gln Asn Ser Lys Arg Asn Gly Gly Ala Thr Arg Thr
        995                 1000                1005

Glu Asn Ser Val Asp Asn Gly Ser Asp Leu Ala Gly Val Thr Asp Gly
    1010                1015                1020

Lys Ala Ala Arg Asn Lys Gly Lys Asn Thr Thr Arg Arg Cys Ala Thr
1025                1030                1035                1040

Cys Gly Gln Ile Gly His Ile Arg Thr Asn Lys Ser Cys Pro Met Tyr
                1045                1050                1055

Ser Ser Lys Asp Asn Pro Ala Ser Pro Lys
            1060                1065
```

( 2 ) INFORMATION FOR SEQ ID NO:2:

( i ) SEQUENCE CHARACTERISTICS:
( A ) LENGTH: 798 amino acids
( B ) TYPE: amino acid
( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
( A ) ORGANISM: S. cerevisiae ( v i i ) IMMEDIATE SOURCE:
( B ) CLONE: TAF-90

( x i ) SEQUENCE DESCRIPTION: SEQ ID NO:2:

```
Met Ser Gln Lys Gln Ser Thr Asn Gln Asn Gln Asn Gly Thr His Gln
1               5                   10                  15

Pro Gln Pro Val Lys Asn Gln Arg Thr Asn Asn Ala Ala Gly Ala Asn
            20                  25                  30

Ser Gly Gln Gln Pro Gln Gln Gln Ser Gln Gly Gln Ser Gln Gln Gln
        35                  40                  45

Gly Arg Ser Asn Gly Pro Phe Ser Ala Ser Asp Leu Asn Arg Ile Val
    50                  55                  60

Leu Glu Tyr Leu Asn Lys Lys Gly Tyr His Arg Thr Glu Ala Met Leu
65                  70                  75                  80

Arg Ala Glu Ser Gly Arg Thr Leu Thr Pro Gln Asn Lys Gln Ser Pro
                85                  90                  95

Ala Asn Thr Lys Thr Gly Lys Phe Pro Glu Gln Ser Ser Ile Pro Pro
            100                 105                 110

Asn Pro Gly Lys Thr Ala Lys Pro Ile Ser Asn Pro Thr Asn Leu Ser
        115                 120                 125

Ser Lys Arg Asp Ala Glu Gly Gly Ile Val Ser Ser Gly Arg Leu Glu
    130                 135                 140

Gly Leu Asn Ala Pro Glu Asn Tyr Ile Arg Ala Tyr Ser Met Leu Lys
145                 150                 155                 160

Asn Trp Val Asp Ser Ser Leu Glu Ile Tyr Lys Pro Glu Leu Ser Tyr
                165                 170                 175

Ile Met Tyr Pro Ile Phe Ile Tyr Leu Phe Leu Asn Leu Val Ala Lys
            180                 185                 190

Asn Pro Val Tyr Ala Arg Arg Phe Phe Asp Arg Phe Ser Pro Asp Phe
        195                 200                 205

Lys Asp Phe His Gly Ser Glu Ile Asn Arg Leu Phe Ser Val Asn Ser
    210                 215                 220
```

```
Ile Asp His Ile Lys Glu Asn Glu Val Ala Ser Ala Phe Gln Ser His
225                 230                 235                 240

Lys Tyr Arg Ile Thr Met Ser Lys Thr Thr Leu Asn Leu Leu Leu Tyr
                245                 250                 255

Phe Leu Asn Glu Asn Glu Ser Ile Gly Gly Ser Leu Ile Ile Ser Val
            260                 265                 270

Ile Asn Gln His Leu Asp Pro Asn Ile Val Glu Ser Val Thr Ala Arg
        275                 280                 285

Glu Lys Leu Ala Asp Gly Ile Lys Val Leu Ser Asp Ser Glu Asn Gly
    290                 295                 300

Asn Gly Lys Gln Asn Leu Glu Met Asn Ser Val Pro Val Lys Leu Gly
305                 310                 315                 320

Pro Phe Pro Lys Asp Glu Glu Phe Val Lys Glu Ile Glu Thr Glu Leu
                325                 330                 335

Lys Ile Lys Asp Asp Gln Glu Lys Gln Leu Asn Gln Gln Thr Ala Gly
            340                 345                 350

Asp Asn Tyr Ser Gly Ala Asn Asn Arg Thr Leu Leu Gln Glu Tyr Lys
        355                 360                 365

Ala Met Asn Asn Glu Lys Phe Lys Asp Asn Thr Gly Asp Asp Asp Lys
    370                 375                 380

Asp Lys Ile Lys Asp Lys Ile Ala Lys Asp Glu Glu Lys Lys Glu Ser
385                 390                 395                 400

Glu Leu Lys Val Asp Gly Glu Lys Lys Asp Ser Asn Leu Ser Ser Pro
                405                 410                 415

Ala Arg Asp Ile Leu Pro Leu Pro Pro Lys Thr Ala Leu Asp Leu Lys
            420                 425                 430

Leu Glu Ile Gln Lys Val Lys Glu Ser Arg Asp Ala Ile Lys Leu Asp
        435                 440                 445

Asn Leu Gln Leu Ala Leu Pro Ser Val Cys Met Tyr Thr Phe Gln Asn
    450                 455                 460

Thr Asn Lys Asp Met Ser Cys Leu Asp Phe Ser Asp Asp Cys Arg Ile
465                 470                 475                 480

Ala Ala Ala Gly Phe Gln Asp Ser Tyr Ile Lys Ile Trp Ser Leu Asp
                485                 490                 495

Gly Ser Ser Leu Asn Asn Pro Asn Ile Ala Leu Asn Asn Asn Asp Lys
            500                 505                 510

Asp Glu Asp Pro Thr Cys Lys Thr Leu Val Gly His Ser Gly Thr Val
        515                 520                 525

Tyr Ser Thr Ser Phe Ser Pro Asp Asn Lys Tyr Leu Leu Ser Gly Ser
    530                 535                 540

Glu Asp Lys Thr Val Arg Leu Trp Ser Met Asp Thr His Thr Ala Leu
545                 550                 555                 560

Val Ser Tyr Lys Gly His Asn His Pro Val Trp Asp Val Ser Phe Ser
                565                 570                 575

Pro Leu Gly His Tyr Phe Ala Thr Ala Ser His Asp Gln Thr Ala Arg
            580                 585                 590

Leu Trp Ser Cys Asp His Ile Tyr Pro Leu Arg Ile Phe Ala Gly His
        595                 600                 605

Leu Asn Asp Val Asp Cys Val Ser Phe His Pro Asn Gly Cys Tyr Val
    610                 615                 620

Phe Thr Gly Ser Ser Asp Lys Thr Cys Arg Met Trp Asp Val Ser Thr
625                 630                 635                 640

Gly Asp Ser Val Arg Leu Phe Leu Gly His Thr Ala Pro Val Ile Ser
                645                 650                 655
```

Ile Ala Val Cys Pro Asp Gly Arg Trp Leu Ser Thr Gly Ser Glu Asp
660 665 670

Gly Ile Ile Asn Val Trp Asp Ile Gly Thr Gly Lys Arg Leu Lys Gln
675 680 685

Met Arg Gly His Gly Lys Asn Ala Ile Tyr Ser Leu Ser Tyr Ser Lys
690 695 700

Glu Gly Asn Val Leu Ile Ser Gly Gly Ala Asp His Thr Val Arg Val
705 710 715 720

Trp Asp Leu Lys Lys Ala Thr Thr Glu Pro Ser Ala Glu Pro Asp Glu
725 730 735

Pro Phe Ile Gly Tyr Leu Gly Asp Val Thr Ala Ser Ile Asn Gln Asp
740 745 750

Ile Lys Glu Tyr Gly Arg Arg Arg Thr Val Ile Pro Thr Ser Asp Leu
755 760 765

Val Ala Ser Phe Tyr Thr Lys Lys Thr Pro Val Phe Lys Val Lys Phe
770 775 780

Ser Arg Ser Asn Leu Ala Leu Ala Gly Gly Ala Phe Arg Pro
785 790 795

( 2 ) INFORMATION FOR SEQ ID NO:3:

( i ) SEQUENCE CHARACTERISTICS:
( A ) LENGTH: 704 amino acids
( B ) TYPE: amino acid
( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
( A ) ORGANISM: D. melanogaster ( v i i ) IMMEDIATE SOURCE:
( B ) CLONE: TAFII-80

( x i ) SEQUENCE DESCRIPTION: SEQ ID NO:3:

Met Ser Leu Glu Val Ser Asn Ile Asn Gly Gly Asn Gly Thr Gln Leu
1 5 10 15

Ser His Asp Lys Arg Glu Leu Leu Cys Leu Leu Lys Leu Ile Lys Lys
20 25 30

Tyr Gln Leu Lys Ser Thr Glu Glu Leu Leu Cys Gln Glu Ala Asn Val
35 40 45

Ser Ser Val Glu Leu Ser Glu Ile Ser Glu Ser Asp Val Gln Gln Val
50 55 60

Leu Gly Ala Val Leu Gly Ala Gly Asp Ala Asn Arg Glu Arg Lys His
65 70 75 80

Val Gln Ser Pro Ala Gln Gly His Lys Gln Ser Ala Val Thr Glu Ala
85 90 95

Asn Ala Ala Glu Glu Leu Ala Lys Phe Ile Asp Asp Asp Ser Phe Asp
100 105 110

Ala Gln His Tyr Glu Gln Ala Tyr Lys Glu Leu Arg Thr Phe Val Glu
115 120 125

Asp Ser Leu Asp Ile Tyr Lys His Glu Leu Ser Met Val Leu Tyr Pro
130 135 140

Ile Leu Val Gln Ile Tyr Phe Lys Ile Leu Ala Ser Gly Leu Arg Glu
145 150 155 160

-continued

```
Lys Ala Lys Glu Phe Ile Glu Lys Tyr Lys Cys Asp Leu Asp Gly Tyr
                165                 170                 175

Tyr Ile Glu Gly Leu Phe Asn Leu Leu Leu Leu Ser Lys Pro Glu Glu
            180                 185                 190

Leu Leu Glu Asn Asp Leu Val Val Ala Met Glu Gln Asp Lys Phe Val
        195                 200                 205

Ile Arg Met Ser Arg Asp Ser His Ser Leu Phe Lys Arg His Ile Gln
    210                 215                 220

Asp Arg Arg Gln Glu Val Val Ala Asp Ile Val Ser Lys Tyr Leu His
225                 230                 235                 240

Phe Asp Thr Tyr Glu Gly Met Ala Arg Asn Lys Leu Gln Cys Val Ala
                245                 250                 255

Thr Ala Gly Ser His Leu Gly Glu Ala Lys Arg Gln Asp Asn Lys Met
            260                 265                 270

Arg Val Tyr Tyr Gly Leu Leu Lys Glu Val Asp Phe Gln Thr Leu Thr
        275                 280                 285

Thr Pro Ala Pro Ala Pro Glu Glu Glu Asp Asp Asp Pro Asp Ala Pro
    290                 295                 300

Asp Arg Pro Lys Lys Lys Lys Pro Lys Lys Asp Pro Leu Leu Ser Lys
305                 310                 315                 320

Lys Ser Lys Ser Asp Pro Asn Ala Pro Ser Ile Asp Arg Ile Pro Leu
                325                 330                 335

Pro Glu Leu Lys Asp Ser Asp Lys Leu Leu Lys Leu Lys Ala Leu Arg
            340                 345                 350

Glu Ala Ser Lys Arg Leu Ala Leu Ser Lys Asp Gln Leu Pro Ser Ala
        355                 360                 365

Val Phe Tyr Thr Val Leu Asn Ser His Gln Gly Val Thr Cys Ala Glu
    370                 375                 380

Ile Ser Asp Asp Ser Thr Met Leu Ala Cys Gly Phe Gly Asp Ser Ser
385                 390                 395                 400

Val Arg Ile Trp Ser Leu Thr Pro Ala Asn Val Arg Thr Leu Lys Asp
                405                 410                 415

Ala Asp Ser Leu Arg Glu Leu Asp Lys Glu Ser Ala Asp Ile Asn Val
            420                 425                 430

Arg Met Leu Asp Asp Arg Ser Gly Glu Val Thr Arg Ser Leu Met Gly
        435                 440                 445

His Thr Gly Pro Val Tyr Arg Cys Ala Phe Ala Pro Glu Met Asn Leu
    450                 455                 460

Leu Leu Ser Cys Ser Glu Asp Ser Thr Ile Arg Leu Trp Ser Leu Leu
465                 470                 475                 480

Thr Trp Ser Cys Val Val Thr Tyr Arg Gly His Val Tyr Pro Val Trp
                485                 490                 495

Asp Val Arg Phe Ala Pro His Gly Tyr Tyr Phe Val Ser Cys Ser Tyr
            500                 505                 510

Asp Lys Thr Ala Arg Leu Trp Ala Thr Asp Ser Asn Gln Ala Leu Arg
        515                 520                 525

Val Phe Val Gly His Leu Ser Asp Val Asp Cys Val Gln Phe His Pro
    530                 535                 540

Asn Ser Asn Tyr Val Ala Thr Gly Ser Ser Asp Arg Thr Val Arg Leu
545                 550                 555                 560

Trp Asp Asn Met Thr Gly Gln Ser Val Arg Leu Met Thr Gly His Lys
                565                 570                 575

Gly Ser Val Ser Ser Leu Ala Phe Ser Ala Cys Gly Arg Tyr Leu Ala
            580                 585                 590
```

Ser Gly Ser Val Asp His Asn Ile Ile Ile Trp Asp Leu Ser Asn Gly
595 600 605

Ser Leu Val Thr Thr Leu Leu Arg His Thr Ser Thr Val Thr Thr Ile
610 615 620

Thr Phe Ser Arg Asp Gly Thr Val Leu Ala Ala Ala Gly Leu Asp Asn
625 630 635 640

Asn Leu Thr Leu Trp Asp Phe His Lys Val Thr Glu Asp Tyr Ile Ser
645 650 655

Asn His Ile Thr Val Ser His His Gln Asp Glu Asn Asp Glu Asp Val
660 665 670

Tyr Leu Met Arg Thr Phe Pro Ser Lys Asn Ser Pro Phe Val Ser Leu
675 680 685

His Phe Thr Arg Arg Asn Leu Leu Met Cys Val Gly Leu Phe Lys Ser
690 695 700

( 2 ) INFORMATION FOR SEQ ID NO:4:

( i ) SEQUENCE CHARACTERISTICS:
( A ) LENGTH: 1377 amino acids
( B ) TYPE: amino acid
( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
( A ) ORGANISM: D. melanogaster ( v i i ) IMMEDIATE SOURCE:
( B ) CLONE: TAFII-250

( x i ) SEQUENCE DESCRIPTION: SEQ ID NO:4:

Met Glu Ser Asp Asn Ser Asp Asp Glu Gly Ser Ile Gly Asn Gly Leu
1 5 10 15

Asp Leu Thr Gly Ile Leu Phe Gly Asn Ile Asp Ser Glu Gly Arg Leu
20 25 30

Leu Gln Asp Asp Asp Gly Glu Gly Arg Gly Gly Thr Gly Phe Asp Ala
35 40 45

Glu Leu Arg Glu Asn Ile Gly Ser Leu Ser Lys Leu Gly Leu Asp Ser
50 55 60

Met Leu Leu Glu Val Ile Asp Leu Lys Glu Ala Glu Pro Pro Ser Asp
65 70 75 80

Asp Glu Glu Glu Glu Asp Ala Arg Pro Ser Ala Val Ser Ala Ser Gly
85 90 95

Gly Met Ser Ala Phe Asp Ala Leu Lys Ala Gly Val Lys Arg Glu Glu
100 105 110

Arg Glu Asp Gly Ala Val Lys Ala Gln Asp Asp Ala Ile Asp Tyr Ser
115 120 125

Asp Ile Thr Glu Leu Ser Glu Asp Cys Pro Arg Thr Pro Pro Glu Glu
130 135 140

Thr Ser Thr Tyr Asp Asp Leu Glu Asp Ala Ile Pro Ala Ser Lys Val
145 150 155 160

Glu Ala Lys Leu Thr Lys Asp Asp Lys Glu Leu Met Pro Pro Pro Ser
165 170 175

Ala Pro Met Arg Ser Gly Ser Gly Gly Gly Ile Glu Glu Pro Ala Lys
180 185 190

-continued

Ser Asn Asp Ala Ser Ser Pro Ser Asp Asp Ser Lys Ser Thr Asp Ser
195 200 205

Lys Asp Ala Asp Arg Lys Leu Asp Thr Pro Leu Ala Asp Ile Leu Pro
210 215 220

Ser Lys Tyr Gln Asn Val Asp Val Arg Glu Leu Phe Pro Asp Phe Arg
225 230 235 240

Pro Gln Lys Val Leu Arg Phe Ser Arg Leu Phe Gly Pro Gly Lys Pro
245 250 255

Thr Ser Leu Pro Gln Ile Trp Arg Glu Val Arg Lys Arg Arg Arg Lys
260 265 270

Arg Asn Gln Ser Arg Asp Gln Lys Thr Thr Asn Thr Gly Gly Ser Asp
275 280 285

Ser Pro Ser Asp Thr Glu Glu Pro Arg Lys Arg Gly Phe Ser Leu His
290 295 300

Tyr Ala Ala Glu Pro Thr Pro Ala Glu Cys Met Ser Asp Asp Glu Asp
305 310 315 320

Lys Leu Leu Gly Asp Phe His Ser Glu Asp Val Arg Pro Phe Gly Pro
325 330 335

Asp Asn Gly Glu Asn Ser Asp Gln Lys Pro Lys Val Ala Asp Trp Arg
340 345 350

Phe Gly Pro Ala Gln Ile Trp Tyr Asp Ile Leu Glu Val Pro Asp Ser
355 360 365

Gly Glu Gly Phe Asn Tyr Gly Phe Lys Thr Lys Ala Ala Ser Thr Ser
370 375 380

Ser Gln Gln Gln Leu Lys Asp Glu Arg Arg Val Lys Ser Pro Glu Asp
385 390 395 400

Asp Val Glu Asp Pro Ser Ile Ala Asp Asp Ala Phe Leu Met Val Ser
405 410 415

Gln Leu His Trp Glu Asp Asp Val Val Trp Asp Gly Asn Asp Ile Lys
420 425 430

Ala Lys Val Leu Gln Lys Leu Asn Ser Lys Thr Asn Ala Ala Gly Trp
435 440 445

Leu Pro Ser Ser Gly Ser Arg Thr Ala Gly Ala Phe Ser Gln Pro Gly
450 455 460

Lys Pro Ser Met Pro Val Gly Ser Gly Ser Ser Lys Gln Gly Ser Gly
465 470 475 480

Ala Ser Ser Lys Lys Ala Gln Gln Asn Ala Gln Ala Lys Pro Ala Glu
485 490 495

Ala Pro Asp Asp Thr Trp Tyr Ser Leu Phe Pro Val Glu Asn Glu Glu
500 505 510

Leu Ile Tyr Tyr Lys Trp Glu Asp Glu Val Ile Trp Asp Ala Gln Gln
515 520 525

Val Ser Lys Val Pro Lys Pro Lys Val Leu Thr Leu Asp Pro Asn Asp
530 535 540

Glu Asn Ile Ile Leu Gly Ile Pro Asp Asp Ile Asp Pro Ser Lys Ile
545 550 555 560

Asn Lys Ser Thr Gly Pro Pro Pro Lys Ile Lys Ile Pro His Pro His
565 570 575

Val Lys Lys Ser Lys Ile Leu Leu Gly Lys Ala Gly Val Ile Asn Val
580 585 590

Leu Ala Glu Asp Thr Pro Pro Pro Pro Pro Lys Ser Pro Asp Arg Asp
595 600 605

Pro Phe Asn Ile Ser Asn Asp Thr Tyr Tyr Thr Pro Lys Thr Glu Pro
610 615 620

```
Thr Leu Arg Leu Lys Val Gly Gly Asn Leu Ile Gln His Ser Thr Pro
625                 630                 635                 640

Val Val Glu Leu Arg Ala Pro Phe Val Pro Thr Arg Met Gly Pro Met
                645                 650                 655

Asn Val Arg Ala Phe His Arg Pro Pro Leu Lys Lys Tyr Ser His Gly
            660                 665                 670

Pro Met Ala Gln Ser Ile Pro His Pro Val Thr Pro Leu Leu Lys Thr
        675                 680                 685

Ile Ala Lys Lys Ala Lys Gln Arg Glu Val Glu Arg Ile Ala Ser Gly
    690                 695                 700

Gly Gly Asp Val Phe Phe Met Arg Asn Pro Glu Asp Leu Ser Gly Arg
705                 710                 715                 720

Asp Gly Asp Ile Val Leu Ala Glu Phe Cys Glu Glu His Pro Pro Leu
                725                 730                 735

Ile Asn Gln Val Gly Met Cys Ser Lys Ile Lys Asn Tyr Tyr Lys Arg
            740                 745                 750

Lys Ala Glu Lys Asp Ser Gly Pro Gln Asp Tyr Val Tyr Gly Glu Val
        755                 760                 765

Ala Phe Ala Arg Thr Ser Pro Phe Leu Gly Ile Leu His Pro Gly Gln
    770                 775                 780

Cys Ile Gln Ala Ile Glu Asn Asn Met Tyr Arg Ala Pro Ile Tyr Pro
785                 790                 795                 800

His Lys Met Ala His Asn Asp Phe Leu Val Ile Arg Thr Arg Asn His
                805                 810                 815

Tyr Trp Ile Arg Ser Val Asn Ser Ile Tyr Thr Val Gly Gln Glu Cys
            820                 825                 830

Pro Leu Tyr Glu Val Pro Gly Pro Asn Ser Lys Arg Ala Asn Asn Phe
        835                 840                 845

Thr Arg Asp Phe Leu Gln Val Thr Ile Tyr Arg Leu Phe Trp Lys Ser
    850                 855                 860

Arg Asp Asn Pro Arg Arg Ile Arg Met Asp Asp Ile Lys Gln Ala Phe
865                 870                 875                 880

Pro Ala His Ser Glu Ser Ser Ile Arg Lys Arg Leu Lys Gln Cys Ala
                885                 890                 895

Asp Phe Lys Arg Thr Gly Met Asp Ser Asn Trp Trp Val Ile Lys Pro
            900                 905                 910

Glu Phe Arg Leu Pro Ser Glu Glu Glu Ile Arg Ala Met Val Ser Pro
        915                 920                 925

Glu Gln Cys Cys Ala Tyr Phe Ser Met Ile Ala Ala Glu Gln Arg Leu
    930                 935                 940

Lys Asp Ala Gly Tyr Gly Glu Lys Phe Leu Phe Ala Pro Gln Glu Asp
945                 950                 955                 960

Asp Asp Glu Glu Ala Gln Leu Lys Leu Asp Asp Glu Val Lys Val Ala
                965                 970                 975

Pro Trp Asn Thr Thr Arg Ala Tyr Ile Gln Ala Met Arg Gly Lys Cys
            980                 985                 990

Leu Leu Gln Leu Ser Gly Pro Ala Asp Pro Thr Gly Cys Gly Glu Gly
        995                 1000                1005

Phe Ser Tyr Val Arg Val Pro Asn Lys Pro Thr Gln Thr Lys Glu Glu
    1010                1015                1020

Gln Glu Ser Gln Pro Lys Arg Ser Val Thr Gly Thr Asp Ala Asp Leu
1025                1030                1035                1040

Arg Arg Leu Pro Leu Gln Arg Ala Lys Glu Leu Leu Arg Gln Phe Lys
```

-continued

```
                    1045                      1050                      1055

Val Pro Glu Glu Glu Ile Lys Lys Leu Ser Arg Trp Glu Val Ile Asp
                1060                1065                1070

Val Val Arg Thr Leu Ser Thr Glu Lys Ala Lys Ala Gly Glu Glu Gly
            1075                1080                1085

Met Asp Lys Phe Ser Arg Gly Asn Arg Phe Ser Ile Ala Glu His Gln
        1090                1095                1100

Glu Arg Tyr Lys Glu Glu Cys Gln Arg Ile Phe Asp Leu Gln Asn Arg
1105                1110                1115                1120

Val Leu Ala Ser Ser Glu Val Leu Ser Thr Asp Glu Ala Glu Ser Ser
                    1125                1130                1135

Ala Ser Glu Glu Ser Asp Leu Glu Glu Leu Gly Lys Asn Leu Glu Asn
                1140                1145                1150

Met Leu Ser Asn Lys Lys Thr Ser Thr Gln Leu Ser Arg Glu Arg Glu
            1155                1160                1165

Glu Leu Glu Arg Gln Glu Leu Leu Arg Gln Leu Asp Glu Glu His Gly
        1170                1175                1180

Gly Pro Ser Gly Ser Gly Gly Ala Lys Gly Ala Lys Gly Lys Asp Asp
1185                1190                1195                1200

Pro Gly Gln Gln Met Leu Ala Thr Asn Asn Gln Gly Arg Ile Leu Arg
                    1205                1210                1215

Ile Thr Arg Thr Phe Arg Gly Asn Asp Gly Lys Glu Tyr Thr Arg Val
                1220                1225                1230

Glu Thr Val Arg Arg Gln Pro Val Ile Asp Ala Tyr Ile Lys Ile Arg
            1235                1240                1245

Thr Thr Lys Asp Glu Gln Phe Ile Lys Gln Phe Ala Thr Leu Asp Glu
        1250                1255                1260

Gln Gln Lys Glu Glu Met Lys Arg Glu Lys Arg Arg Ile Gln Glu Gln
1265                1270                1275                1280

Leu Arg Arg Ile Lys Arg Asn Gln Glu Arg Glu Arg Leu Ala Gln Leu
                    1285                1290                1295

Ala Gln Asn Gln Lys Leu Gln Pro Gly Gly Met Pro Thr Ser Leu Gly
                1300                1305                1310

Asp Pro Lys Ser Ser Gly Gly His Ser His Lys Glu Arg Asp Ser Gly
            1315                1320                1325

Tyr Lys Glu Val Ser Pro Ser Arg Lys Lys Phe Lys Leu Lys Pro Asp
        1330                1335                1340

Leu Lys Leu Lys Cys Gly Ala Cys Gly Gln Val Gly His Met Arg Thr
1345                1350                1355                1360

Asn Lys Ala Cys Pro Leu Tyr Ser Gly Met Gln Ser Ser Leu Ser Gln
                    1365                1370                1375

Ser
```

( 2 ) INFORMATION FOR SEQ ID NO:5:

( i ) SEQUENCE CHARACTERISTICS:
( A ) LENGTH: 22 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: S. cerevisiae ( v i i ) IMMEDIATE SOURCE:
( B ) CLONE: TAF-90 PEPTIDE 1

( x i ) SEQUENCE DESCRIPTION: SEQ ID NO:5:

Ala Thr Thr Glu Pro Ser Ala Glu Pro Asp Glu Pro Phe Ile Gly Tyr
1 5 10 15

Leu Gly Asp Val Thr Ala
20

( 2 ) INFORMATION FOR SEQ ID NO:6:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: S. cerevisiae ( v i i ) IMMEDIATE SOURCE:
( B ) CLONE: TAF-90 PRIMER 1

( x i ) SEQUENCE DESCRIPTION: SEQ ID NO:6:

AGATACTTGA AAATCTAGAA TGTCACAC 28

( 2 ) INFORMATION FOR SEQ ID NO:7:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: S. cerevisiae ( v i i ) IMMEDIATE SOURCE:
( B ) CLONE: TAF-90 PRIMER 2

( x i ) SEQUENCE DESCRIPTION: SEQ ID NO:7:

GGTTATACTT ATTACATATC ACTTCCATGC 30

( 2 ) INFORMATION FOR SEQ ID NO:8:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( v ) FRAGMENT TYPE: internal ( v i ) ORIGINAL SOURCE:
( A ) ORGANISM: S. cerevisiae ( v i i ) IMMEDIATE SOURCE:
( B ) CLONE: TAF-145 PEPTIDE 1

( x i ) SEQUENCE DESCRIPTION: SEQ ID NO:8:

Asn Ile Asn His Leu Phe Thr Val Gly Gln Thr Phe Pro Val Glu Glu
1 5 10 15

Ile Pro Gly Pro Asn
20

-continued ( 2 ) INFORMATION FOR SEQ ID NO:9:

( i ) SEQUENCE CHARACTERISTICS:
( A ) LENGTH: 17 amino acids
( B ) TYPE: amino acid
( D ) TOPOLOGY: linear ( i i ) MOLECULE TYPE: peptide ( v ) FRAGMENT TYPE: internal ( v i ) ORIGINAL SOURCE:
( A ) ORGANISM: S. cerevisiae ( v i i ) IMMEDIATE SOURCE:
( B ) CLONE: TAF-145 PEPTIDE 2

( x i ) SEQUENCE DESCRIPTION: SEQ ID NO:9:

```
Leu Pro Val Gly Glu Thr His Val Leu Gly Val Gln Asp Lys Ser Pro
1               5                   10                  15

Phe
```

( 2 ) INFORMATION FOR SEQ ID NO:10:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: S. cerevisiae ( v i i ) IMMEDIATE SOURCE:
( B ) CLONE: TAF-145 PRIMER 1

( x i ) SEQUENCE DESCRIPTION: SEQ ID NO:10:

```
TTYCCNGTNG ARGARAT                                    17
```

( 2 ) INFORMATION FOR SEQ ID NO:11:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: S. cerevisiae ( v i i ) IMMEDIATE SOURCE:
( B ) CLONE: TAF-145 PRIMER 2

( x i ) SEQUENCE DESCRIPTION: SEQ ID NO:11:

```
GTNGGNGARA CNCAYGT                                    17
```